(12) United States Patent
Van Wyk et al.

(10) Patent No.: US 8,475,452 B2
(45) Date of Patent: Jul. 2, 2013

(54) INSTRUMENTS AND METHODS FOR THERMAL TISSUE TREATMENT

(75) Inventors: Robert A. Van Wyk, Largo, FL (US); Yuval Carmel, Rockville, MD (US); Anatoly Shkvarunets, Rockville, MD (US)

(73) Assignee: ElectroMedical Associates, LLC, Bethesda, MD (US)

( * ) Notice: Subject to any disclaimer, the term of this patent is extended or adjusted under 35 U.S.C. 154(b) by 1220 days.

(21) Appl. No.: 12/033,987

(22) Filed: Feb. 20, 2008

(65) Prior Publication Data

US 2008/0208189 A1    Aug. 28, 2008

Related U.S. Application Data

(60) Provisional application No. 60/902,548, filed on Feb. 21, 2007.

(51) Int. Cl.
    *A61B 18/14* (2006.01)
(52) U.S. Cl.
    USPC .............................................. 606/50; 606/41
(58) Field of Classification Search
    USPC ........................................ 606/41–42, 45, 49
    See application file for complete search history.

(56) References Cited

U.S. PATENT DOCUMENTS

| | | | |
|---|---|---|---|
| 2,448,741 A | 9/1948 | Scott et al. | |
| 3,856,015 A | 12/1974 | Iglesias | |
| 3,901,242 A | 8/1975 | Storz | |
| 4,674,499 A | 6/1987 | Pao | |
| 4,682,596 A | 7/1987 | Bales | |
| 4,726,370 A | 2/1988 | Karasawa | |
| 4,917,082 A | 4/1990 | Grossi et al. | |
| 5,195,959 A | 3/1993 | Smith | |
| 5,277,696 A | 1/1994 | Hagen | |
| 5,314,459 A | 5/1994 | Swanson | |
| 5,782,829 A | 7/1998 | Swiantek | |
| 6,033,400 A | 3/2000 | Grossi et al. | |
| 6,066,134 A | 5/2000 | Eggers | |
| 6,113,597 A | 9/2000 | Eggers et al. | |
| 6,169,926 B1 | 1/2001 | Baker | |
| 6,197,025 B1 | 3/2001 | Grossi et al. | |
| 6,391,025 B1 | 5/2002 | Weinstein et al. | |
| 6,419,684 B1 | 7/2002 | Heisler et al. | |
| 6,565,560 B1 | 5/2003 | Goble et al. | |
| 6,575,968 B1 | 6/2003 | Eggers | |
| 6,796,982 B2 | 9/2004 | Carmel et al. | |
| 6,840,937 B2 | 1/2005 | Van Wyk | |
| 6,899,712 B2 | 5/2005 | Moustafis et al. | |
| 6,921,398 B2 | 7/2005 | Carmel et al. | |
| 6,921,399 B2 | 7/2005 | Carmel et al. | |
| 6,955,676 B2 | 10/2005 | Quick | |
| 7,066,936 B2 | 6/2006 | Ryan | |
| 7,166,103 B2 | 1/2007 | Carmel et al. | |
| 2002/0038122 A1 | 3/2002 | Peters et al. | |

(Continued)

*Primary Examiner* — Michael Peffley
*Assistant Examiner* — Samantha Good
(74) *Attorney, Agent, or Firm* — Chalin A. Smith; Smith Patent Consulting

(57) ABSTRACT

Disclosed herein are high efficiency surgical devices and methods of using same using radio frequency (RF) electrical power and/or electrically heated filaments to destroy tumors, form lesions, denaturize, desiccate, coagulate and ablate soft tissues, as well as to drill, cut, resect and vaporize soft tissues. According to the principles of this invention, the electrosurgical instruments can be used with externally supplied conductive or non-conductive liquids, as well as without externally supplied liquids, a mode of operation often referred to as "dry field" environment.

24 Claims, 30 Drawing Sheets

U.S. PATENT DOCUMENTS

| | | |
|---|---|---|
| 2004/0030330 A1 | 2/2004 | Brassel et al. |
| 2004/0049183 A1 | 3/2004 | Ellman et al. |
| 2004/0106919 A1 | 6/2004 | Hood |
| 2004/0193150 A1 | 9/2004 | Sharkey et al. |
| 2005/0065510 A1* | 3/2005 | Carmel et al. ............ 606/41 |
| 2005/0234446 A1 | 10/2005 | Van Wyk et al. |
| 2006/0224154 A1 | 10/2006 | Shadduck et al. |
| 2006/0259031 A1 | 11/2006 | Carmel et al. |
| 2006/0293653 A1 | 12/2006 | Van Wyk |

* cited by examiner

SECTION A-A

SECTION B-B

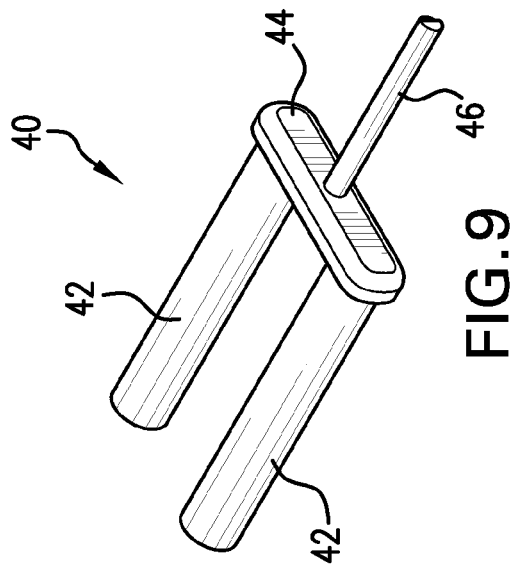
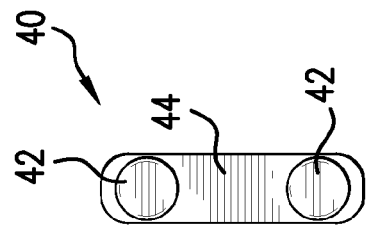
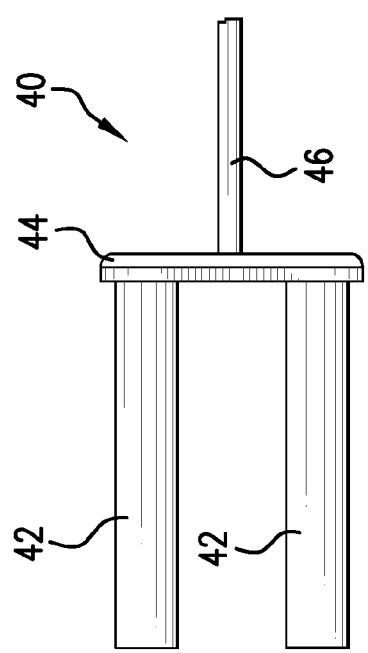
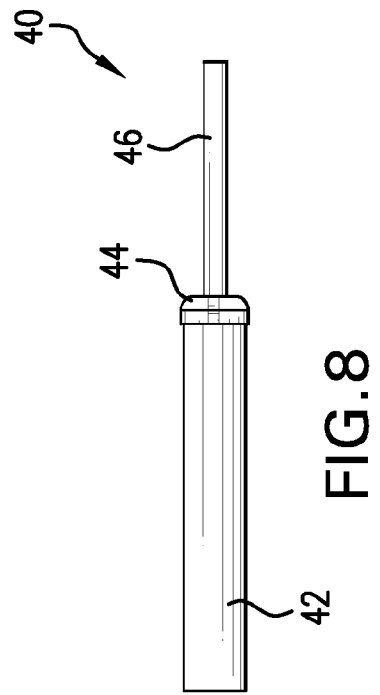

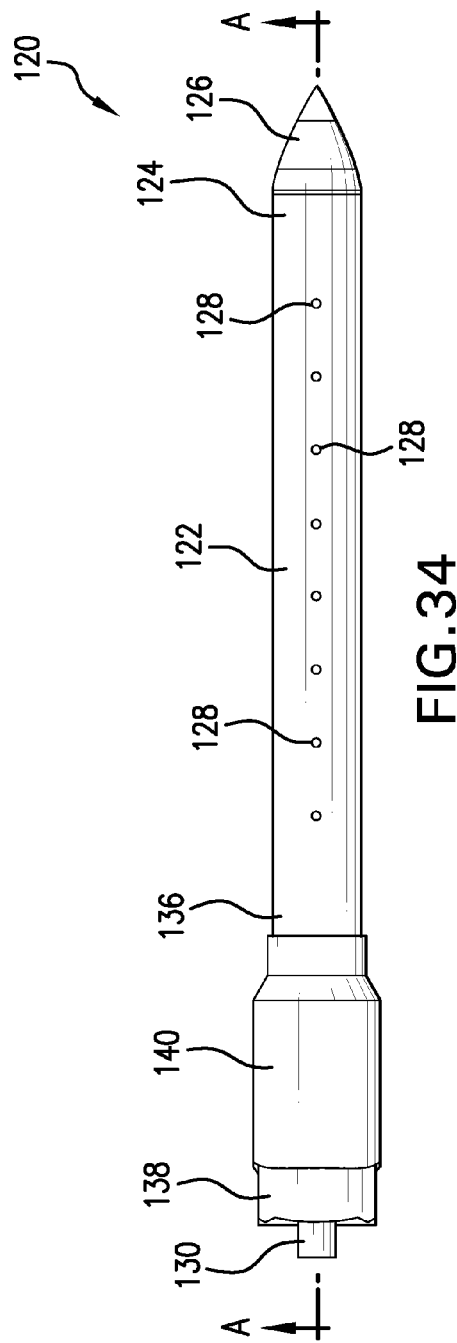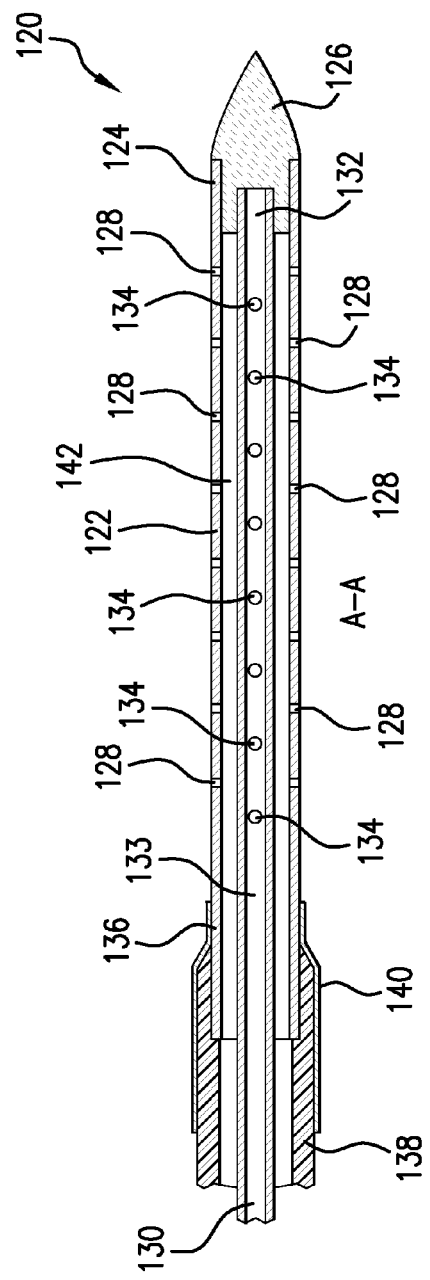
FIG.34
FIG.35

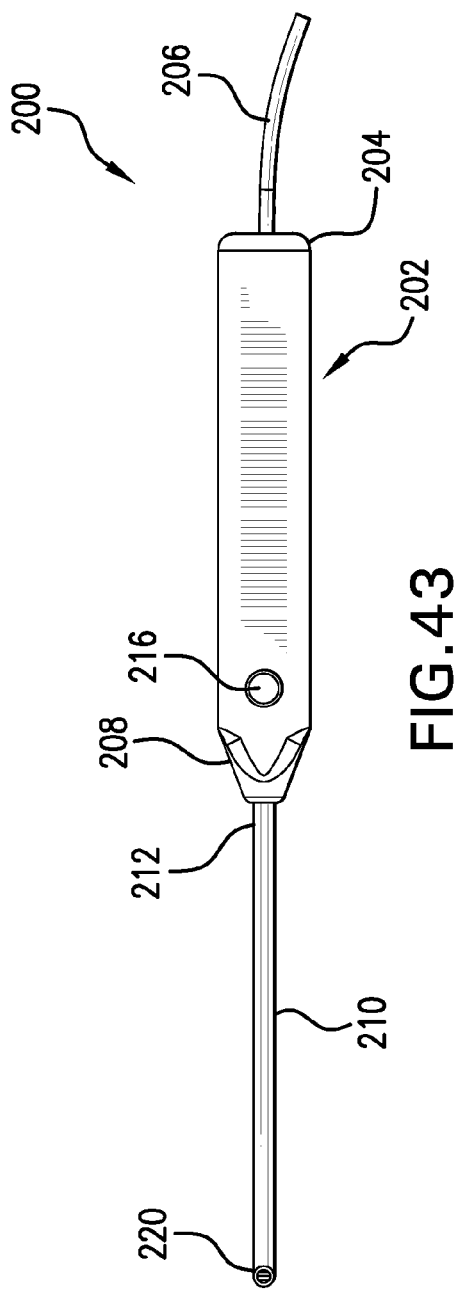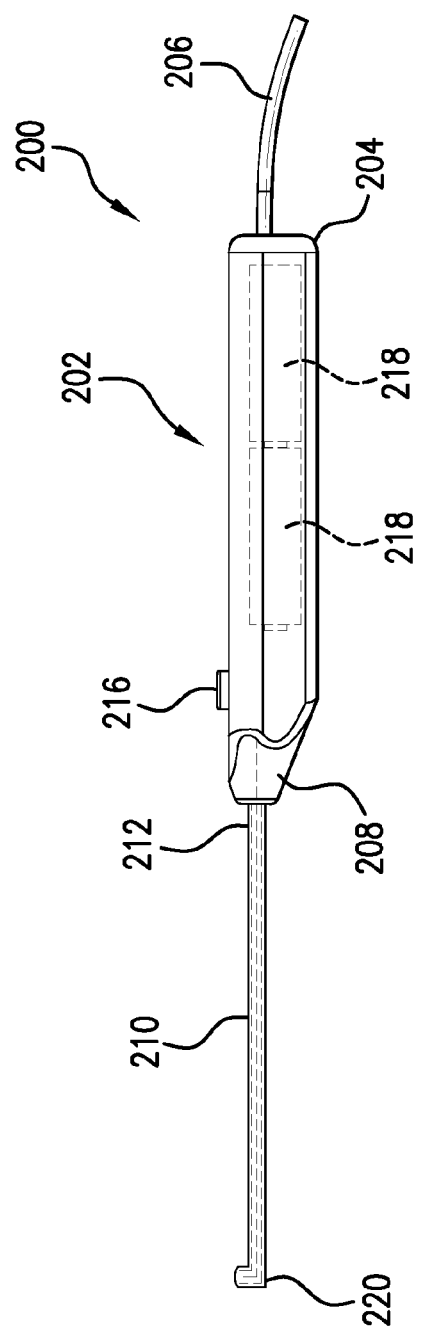
FIG. 43
FIG. 44

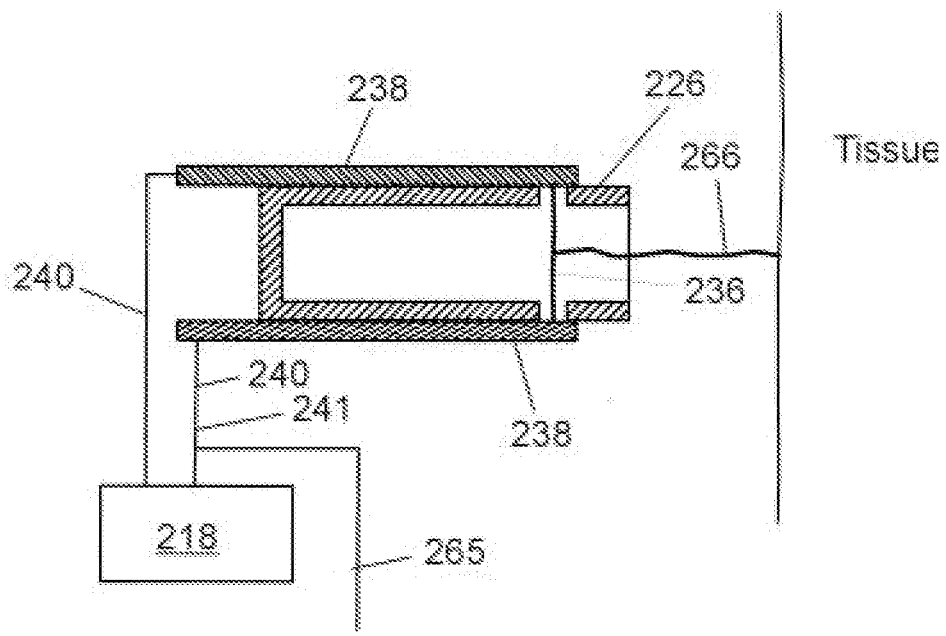
(A)
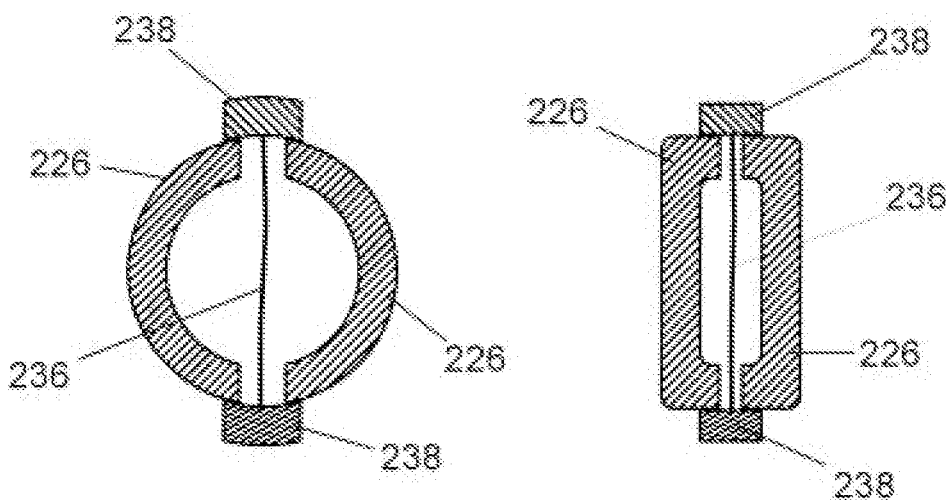
(B) (C)
Fig. 52

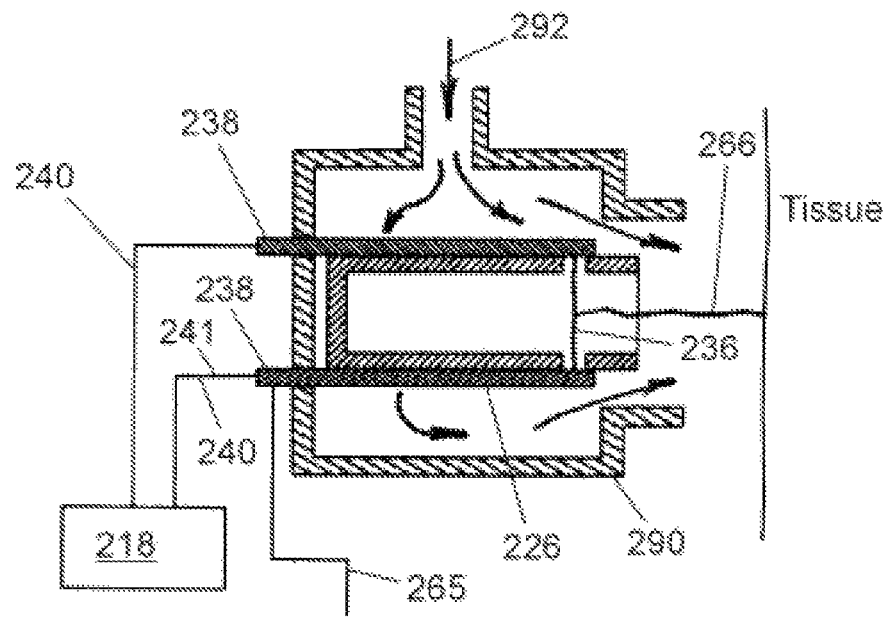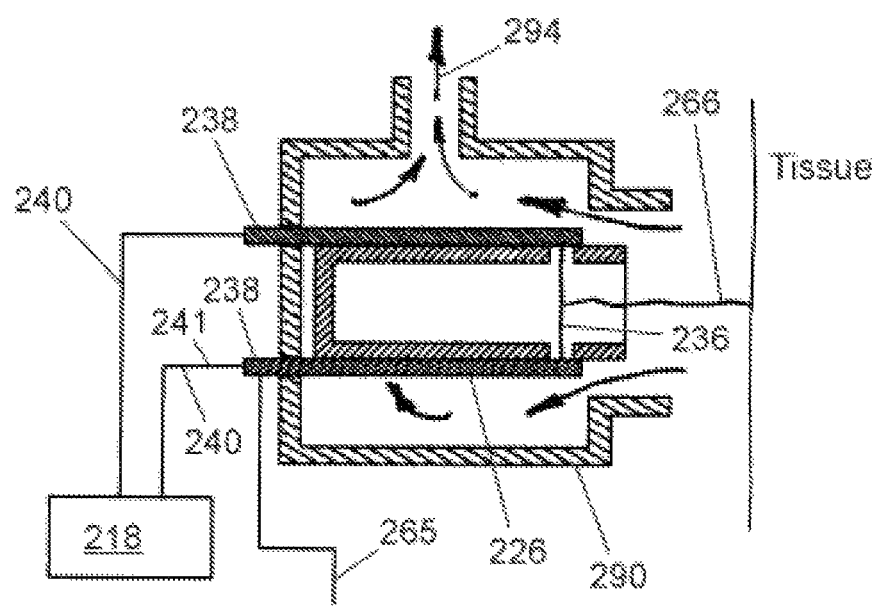
Fig. 60

INSTRUMENTS AND METHODS FOR THERMAL TISSUE TREATMENT

PRIORITY

This application claims the benefit of U.S. Provisional Application No. 60/902,548 filed Feb. 21, 2007, the entire contents of which are incorporated by reference herein.

FIELD OF THE INVENTION

The present invention relates generally to the field of thermal tissue treatment, and more particularly, to high efficiency surgical instruments and methods which use radio frequency (RF) electrical power and/or electrically heated filaments to destroy tumors, form lesions, denaturize, desiccate, coagulate and ablate soft tissues, as well as to drill, cut, resect and vaporize soft tissues. According to the principles of this invention, the electrosurgical instruments of the present invention can be used to thermally treat target tissues of interest, either at the tissue surface, below the tissue surface or at a site remote therefrom, using externally supplied conductive or non-conductive fluids, as well as without externally supplied liquids, a mode of operation often referred to as "dry field" environment.

BACKGROUND OF THE INVENTION

Electrosurgical procedures are advantageous since they generally reduce patient bleeding and trauma. The devices used are electrically energized, typically using an RF generator operating at a frequency that ranges between 100 kHz to over 4 MHz. Due to their ability to provide beneficial outcomes with reduced patient pain and recuperation time, electrosurgical devices have recently gained significant popularity recently. In common terminology and as used herein, the term "electrode" can refer to one or more components of an electrosurgical device (such as an "active electrode" or a "return electrode") or to the entire device, as in an "ablator electrode" or "cutting electrode". Electrosurgical devices may also be referred to as electrosurgical "probes" or "instruments".

Many types of electrosurgical instruments are currently in use, and can be divided into two general categories: monopolar devices and bipolar devices. In the context of monopolar electrosurgical devices, the RF current generally flows from an exposed active electrode, through the patient's body, to a passive, return current electrode that is externally attached to a suitable location on the patient body. In this manner, the patient's body becomes part of the return current circuit. In the context of bipolar electrosurgical devices, both the active and the return current electrodes are exposed, and are typically positioned in close proximity to each other, more frequently mounted on the same instrument. The RF current flows from the active electrode to the return electrode through the nearby tissue and conductive fluids.

The need to effectively yet minimally invasively treat tumor tissue from a patient's body arises in the context of many medical practice areas, including, but not limited to, oncology, ear nose and throat (ENT), urology, gynecology, laparoscopy and general surgery. More specifically, there is often a need to denaturize, desiccate or coagulate tissue and destroy tumors in the liver, kidney, breast, lung, bone, lymph nodes, nerve ganglia and other organs. Such procedures are collectively referred to as tissue ablation or lesion formation, and are often used to destroy tumors without radical surgery. In such cases, an effective treatment is one in which the tumor itself, and perhaps a small margin of tissue around the tumor, is affected. The affected tumor tissue is not immediately removed. Over time, the dead tissue will naturally shrink, dissolve and, in some cases, be gradually replaced by scar tissue.

Although the benefits of these procedures are well recognized by those of skill in the art, current electrosurgical instruments and procedures suffer from very significant deficiencies. Quite often existing instruments are composed of one or more needles which are electrically energized by radiofrequency. As a result, the energy deposition in the tissue is concentrated close to where the needle is positioned, leading to overheating in the immediate region and under-heating in areas farther away. The result is a highly non-homogeneous energy deposition and highly non-homogeneous lesion. It is inherently impossible to accurately control the shape and size of the lesion formed with existing instruments because the energy deposition and heating occurs from the inside out. However, in order to destroy a tumor, it is often necessary, yet undesirable, to also destroy a large margin of healthy tissue around the tumor. As a result the current processes are inefficient, require high power levels and therefore can lead to unnecessary complications and undesired side effects. In some cases, additional return electrodes (also called grounding pads or patient electrodes) are needed in order to safely handle the high energy and high current required to perform the procedure. One such system marketed by Boston Scientific (Natick, Mass.) for lever ablation uses four patient electrodes simultaneously.

In view of these and other deficiencies, there is a need in the art for improved electrosurgical instruments that are capable of creating uniform lesions of a desired size and shape, capable of treating tissue and tumors from the outside in rather than from the inside out, and capable of treating large and non uniform tumors and leaving healthy tissue unharmed. There is also a need in the art for a high efficiency electrosurgical instrument capable of destroying the tumor at relatively low power, thereby increasing patient safety and efficacy and reducing undesired side effects.

SUMMARY OF THE INVENTION

It is accordingly an object of the present invention to provide a highly efficient, minimally invasive surgical instrument capable of overcoming the deficiencies discussed above. More particularly, in view of the ever-present need in the art for improvements in electrode design, it is an object of the present invention to provide a highly efficient and efficacious electrosurgical instrument suitable for the thermal treatment of tumors, more particularly a radiofrequency electrosurgical device adapted for enhanced lesion formation.

Electrosurgical instruments of the present invention may be designed to be inserted directly, to penetrate the patient tissue at the desired location, or alternatively to be introduced into the patient body through a cannula, a resectoscope, an endoscope or an opening in the body.

In certain embodiments, the electrosurgical instruments of the present invention may optionally be provided with means for externally supplying irrigation liquid, either electrically conductive or non-conductive, to the surgical site. In other embodiments, the electrosurgical instrument of the present invention may be designed to function in the absence of an external source of fluids, relying instead on the tissue properties or endogenous bodily fluids. As noted above, this mode of operation is sometimes referred to as "dry field".

In further embodiments, the electrosurgical instrument of the present invention may optionally be equipped with irrigation, aspiration or both, as well as oscillatory or imitational motion.

The electrosurgical instrument of the present invention may be either monopolar or bipolar electrodes and may optionally be equipped with one or more floating elements. "Floating" electrodes for electrosurgery are described in co-pending U.S. patent application Ser. Nos. 10/911,309 (published as US 2005-0065510) and 11/136,514 (published as US 2005-023446), the contents of which are incorporated by reference herein in their entirety.

In yet further embodiments, the electrosurgical instrument of the present invention may include an advanced active electrode designed to operate at high temperatures for improved efficiency.

In yet further embodiments, the electrosurgical instrument of the present invention may be provided with one or more high-powered sources of non-coherent radiation to affect tissue surfaces.

In yet further embodiments, the electrosurgical instrument of the present invention may be designed to operate without contact between the electrode and the tissue surface.

It will be understood by those skilled in the art that one or more aspects of this invention can meet certain objectives, while one or more other aspects can meet certain other objectives. Each objective may not apply equally, in all its respects, to every aspect of this invention. As such, the following objects should be viewed in the alternative with respect to any one aspect of this invention:

Thus, it is an object of the present invention to provide an electrosurgical instrument for thermal tissue treatment composed of:
 (a) an elongate shaft having a proximal end configured for connection to a power source and a distal end having an electrode assembly mounted thereto;
 (b) an electrode assembly comprising an active electrode, a floating electrode, and an insulator separating the active and floating electrodes and defining a cavity therebetween;
 (c) a means for supplying an irrigant to the cavity;
wherein the insulator is formed from a nonconductive dielectric material while said active and floating electrodes are formed from an electrically conductive material;
wherein the active and floating electrodes are positioned in close proximity to each other;
wherein the active electrode is connected via cabling disposed within said shaft to said power source while the floating electrode is not connected to a power source such that powering of the active electrode results in flow of current from the active electrode to said floating electrode via the irrigant, thereby resulting in the heating of the irrigant and the generation of steam;
wherein the heated irrigant and steam contacts target tissue so as to thermally treat the target tissue of interest.

It is a further object of the present invention to provide an electrosurgical instrument for sub-surface thermal treatment of target tissue composed of:
 (a) an elongate shaft having a proximal end configured for connection to a power source and a distal end having an electrode assembly mounted thereto;
 (b) an electrode assembly including (i) an insulating tubular member, (ii) an active electrode disposed at the distal tip of the insulating tubular member and connected via cabling disposed within the shaft to said power source, and (iii) a tubular conductive member concentrically disposed about the insulating tubular member; and
 (c) a switching means for alternately connecting and disconnecting the conductive member to a power source;
wherein the insulating tubular member is formed from a nonconductive dielectric material while the active electrode and said conductive member are formed from an electrically conductive material;
wherein the active and floating electrodes are positioned in close proximity to each other but are prevented by the insulator from directly contacting each other; and
wherein the active electrode takes the form of a tapered conical member that is sufficiently sharp to permit insertion of the electrode assembly into the target tissue.

It is yet a further object of the present invention to provide a method for thermally treating a target tissue in the body of a patient including the steps of:
 (a) introducing an electrosurgical instrument the present invention into the patient such that the electrode assembly is in close contact with the target tissue;
 (b) supplying an irrigant to the cavity defined between the active and floating electrodes; and
 (c) applying a high-frequency voltage to the active electrode;
wherein the high frequency voltage results not only in the flow of current among active electrode, floating electrode and target tissue but further results in the boiling of irrigant, such that expanding steam and heated irrigant flow from the cavity to the target tissue site, thereby thermally treating the target tissue.

The present invention relates generally to the field of thermal tissue treatment, and more particularly, to high efficiency surgical instruments and methods which use radio frequency (RF) electrical power and/or electrically heated filaments to destroy tumors, form lesions, denaturize, desiccate, coagulate and ablate soft tissues, as well as to drill, cut, resect and vaporize soft tissues. According to the principles of this invention, the surgical instruments of the present invention can be used with externally supplied conductive or non-conductive liquids, as well as without externally supplied liquids, a mode of operation often referred to as "dry field" environment.

In one embodiment, the present invention provides a high efficiency electrosurgical instrument particularly suited to surface treatment of tissues, such a tumor tissues, the instrument including an active end having radiused corners and composed of a unique combination of active electrode, insulator, floating electrode and return electrode that limit sparking and tissue vaporization. Illustrative examples of this object are set forth in FIGS. 1-22.

In another embodiment, the present invention provides a high efficiency electrosurgical instrument wherein the active electrode and floating electrode interact to boil an exogenous irrigant therebetween such that lesion formation is accomplished primarily by steam and heated fluid which contact the tissue. Illustrative examples of this object are set forth in FIGS. 23-29.

In yet another embodiment, the present invention provides a high efficiency electrosurgical instrument particularly suited to sub-surface tissue treatment, the instrument including a switching means that allows a circumferential electrode to function as a floating electrode when drilling into the tissue, and subsequently as an active electrode to thermally treat tissue when in close proximity to a target site. Illustrative examples of this object are set forth in FIGS. 30-32.

In a further embodiment, the present invention provides a high efficiency electrosurgical instrument particularly suited to sub-surface tissue treatment, wherein the instrument uses heated irrigant and steam generated within the probe to thermally treat tissue in close proximity. In one embodiment, the heating occurs within the instrument tip, between an active tip electrode and a floating electrode in contact with the tissue. Illustrative examples of this object are set forth in FIGS. 33-36.

In yet a further embodiment, the present invention provides a high efficiency electrosurgical instrument particularly suited to sub-surface tissue treatment, the instrument including an active electrode is inserted into the tissue and a return electrode positioned on the surface of the organ in close proximity to the active electrode so as to focus the current flow in the desired region. Illustrative examples of this object are set forth in FIGS. 37-38.

In yet a further embodiment, the present invention provides a high efficiency electrosurgical instrument particularly suited to thermal tissue treatment, the instrument composed of a monopolar probe with low-flow irrigation to prevent tissue charring. Illustrative examples of this object are set forth in FIGS. 39-41.

In yet a further embodiment, the present invention provides a high efficiency electrosurgical instrument particularly suited to thermal tissue treatment, wherein the instrument includes a heated filament to generate plasma channels between the filament and the surface. Illustrative examples of this object are set forth in FIGS. 42-60.

In yet a further embodiment, the present invention provides a minimally invasive instrument particularly suited to thermal tissue treatment, wherein the instrument includes a heated filament emitting electromagnetic radiation in the form of a non-coherent infra-red, ultraviolet and/or visible spectrum to achieve thermal surface treatment and lesion formation. Illustrative examples of this object are set forth in FIGS. 61-62.

These and other objects and features of the invention will become more fully apparent when the following detailed description is read in conjunction with the accompanying figures and/or examples. However, it is to be understood that both the foregoing summary of the invention and the following detailed description are of a preferred embodiment and not restrictive of the invention or other alternate embodiments of the invention. In particular, while the invention is described herein with reference to a number of specific embodiments, it will be appreciated that the description is illustrative of the invention and is not constructed as limiting of the invention. Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of electrode design. Such objects, features, benefits and advantages will be apparent from the above in conjunction with the accompanying examples, data, figures and all reasonable inferences to be drawn there-from, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments which follows:

FIG. 7 is a plan view of an active electrode for a lesion forming electrosurgical instrument formed in accordance with the principles of this invention.

FIG. 8 is a side elevational view of the objects of FIG. 7.

FIG. 9 is a perspective view of the objects of FIG. 7.

FIG. 10 is a distal axial view of the objects of FIG. 7.

FIG. 34 is a plan view of the objects of FIG. 33.

FIG. 35 is a side elevational sectional view of the objects of FIG. 34 at location A-A of FIG. 34.

FIG. 43 is a plan view of the objects of FIG. 42.

FIG. 44 is a side elevational view of the objects of FIG. 42.

FIG. 52(a) is a schematic representation of the distal end portion of the instrument of FIG. 42. FIG. 52(b) is an axial sectional view of the objects of FIG. 51(a) at location A-A of FIG. 51(a). FIG. 52(c) is an axial sectional view of an alternate embodiment at location A-A of FIG. 51(a).

FIG. 60(a) is a schematic representation of a distal portion of an alternate embodiment which is configured for gas flow outward from the instrument tip. FIG. 60(b) is a schematic representation of a distal portion of an alternate embodiment which is configured for gas flow inward from the instrument tip.

DESCRIPTION OF THE PREFERRED EMBODIMENTS

Figure 1:
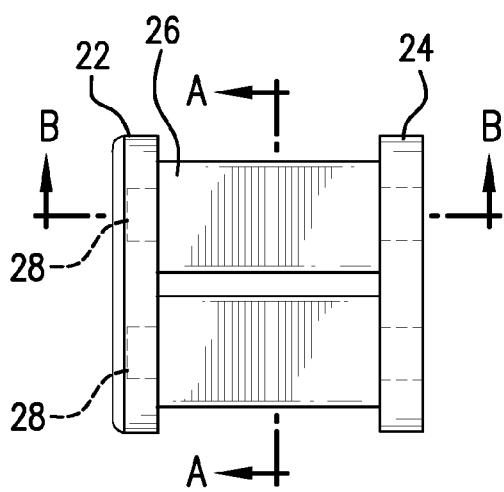
FIG. 1 is a plan view of an insulator for a lesion forming electrosurgical instrument formed in accordance with the principles of this invention.
Figure 4:
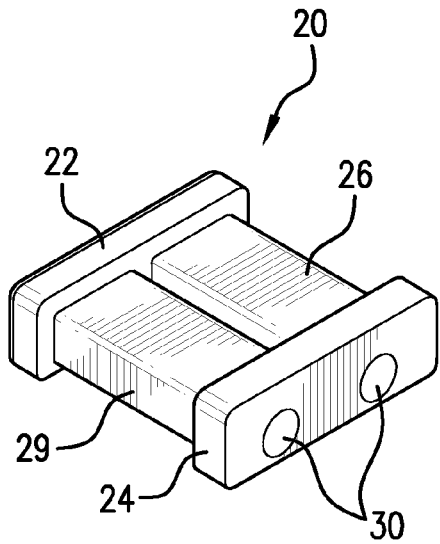
FIG. 4 is a perspective view of the objects of FIG. 1.
Figure 2:
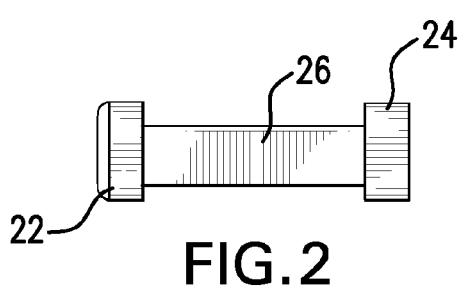
FIG. 2 is a side elevational view of the objects of FIG. 1.
Figure 5:
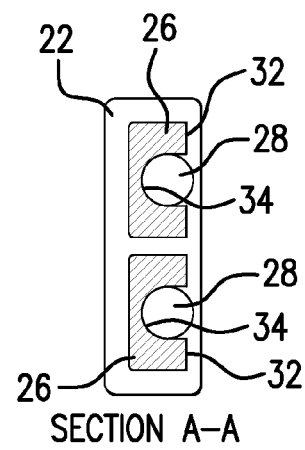
FIG. 5 is an axial sectional view of the objects of FIG. 1 at location A-A of FIG. 1.
Figure 3:
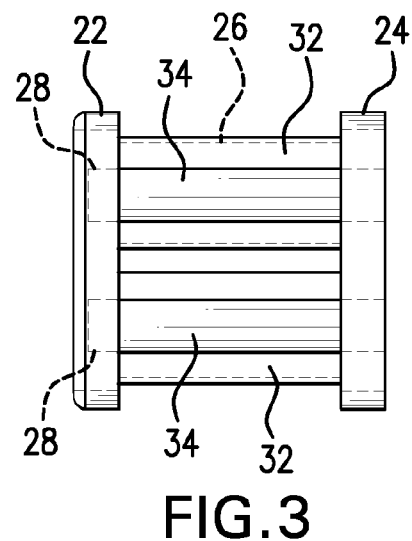
FIG. 3 is a bottom side plan view of the objects of FIG. 1.
Figure 6:
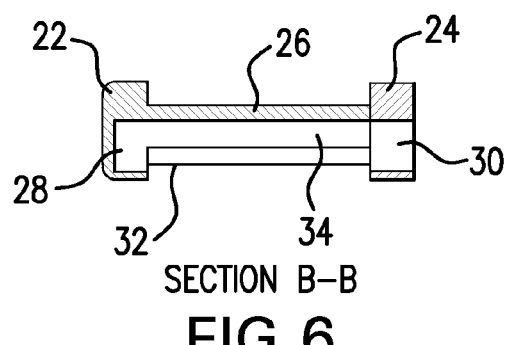
FIG. 6 is a side elevational sectional view of the objects of FIG. 1 at location B-B of FIG. 1.
Figure 11:
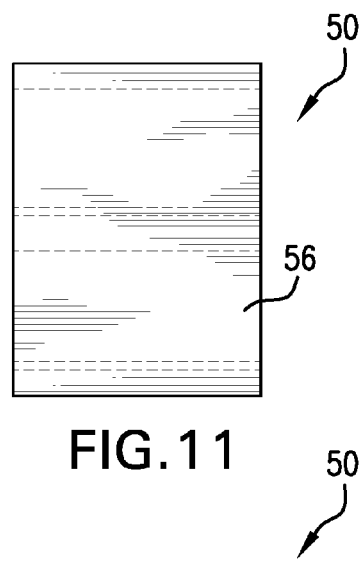
FIG. 11 is a plan view of a floating electrode for a lesion forming electrosurgical instrument formed in accordance with the principles of this invention.
Figure 12:
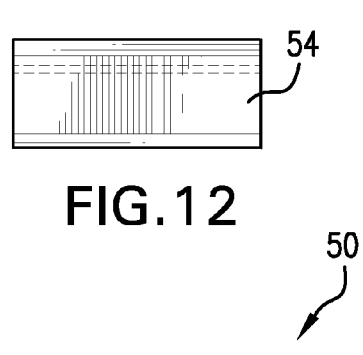
FIG. 12 is a side elevational view of the objects of FIG. 11.
Figure 13:
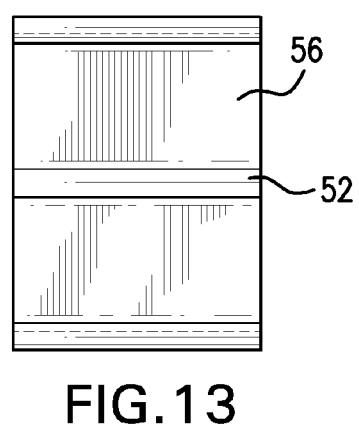
FIG. 13 is a bottom side plan view of the objects of FIG. 11.
Figure 14:
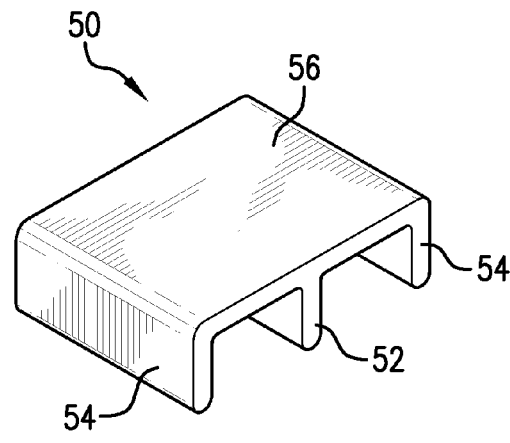
FIG. 14 is a perspective view of the objects of FIG. 11.
Figure 15:
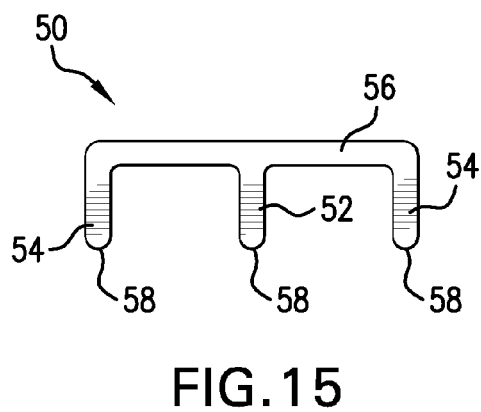
FIG. 15 is an axial view of the objects of FIG. 11.
Figure 16:
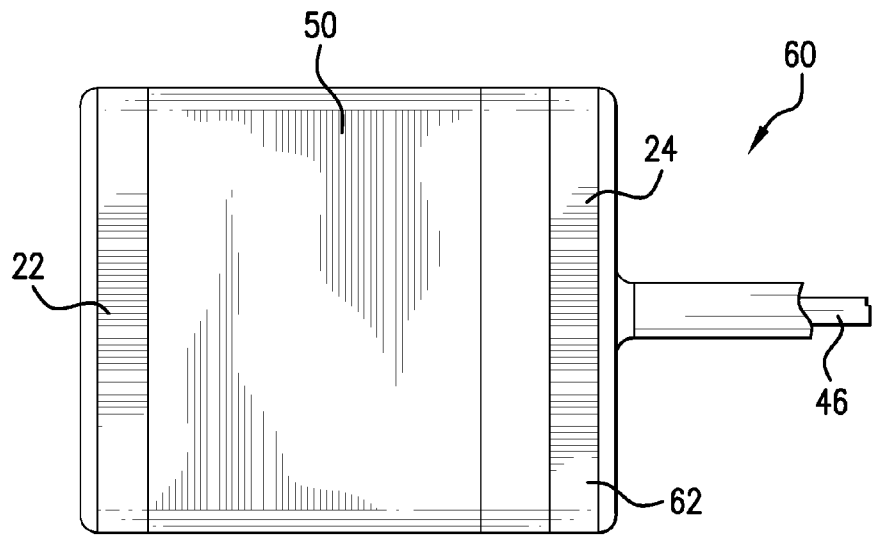
FIG. 16 is a plan view of a distal portion of a lesion forming electrosurgical instrument formed in accordance with the principles of this invention.
Figure 17:
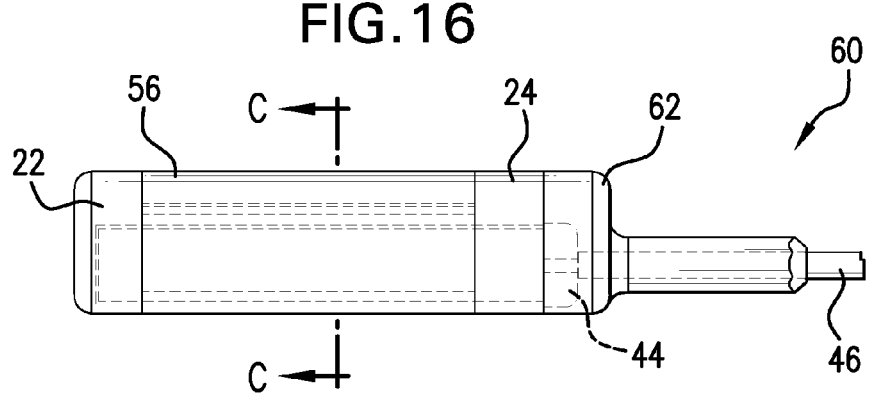
FIG. 17 is a side elevational view of the objects of FIG. 16.
Figure 18:
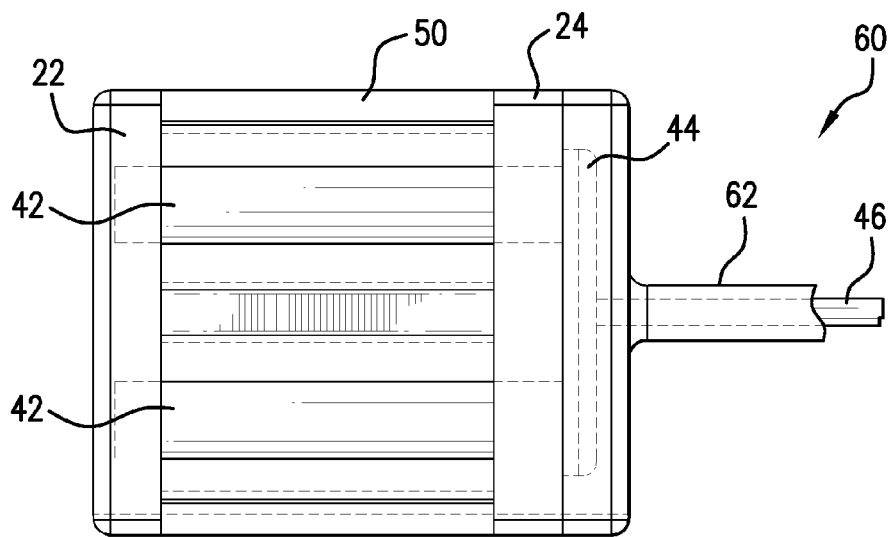
FIG. 18 is a bottom side plan view of the objects of FIG. 16.
Figure 19:
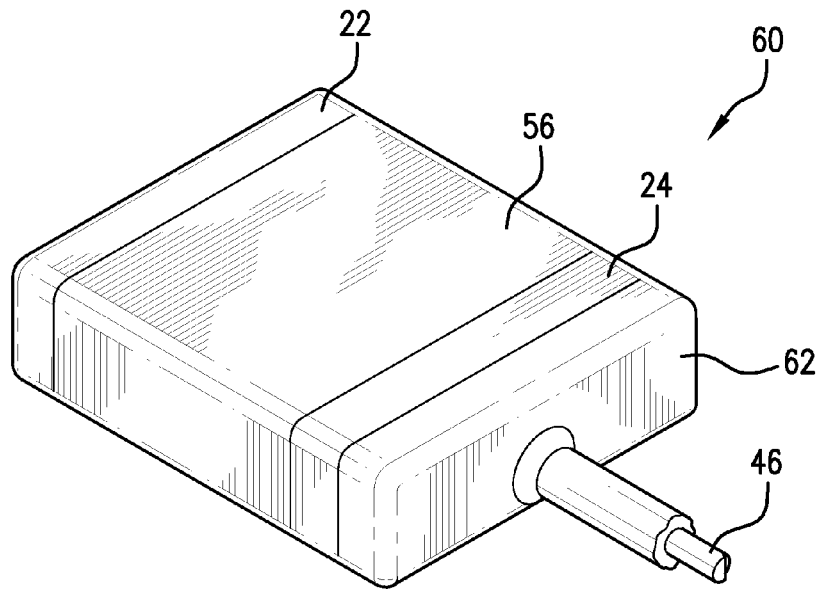
FIG. 19 is a perspective view of the objects of FIG. 16.
Figure 20:
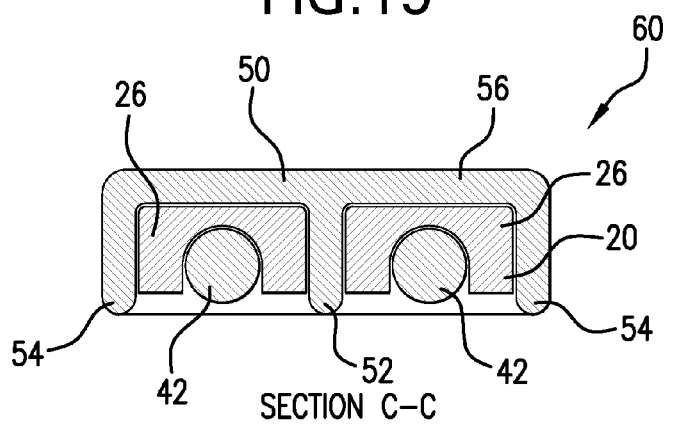
FIG. 20 is an axial sectional view of the objects of FIG. 16 at location C-C of FIG. 17.
Figure 21:
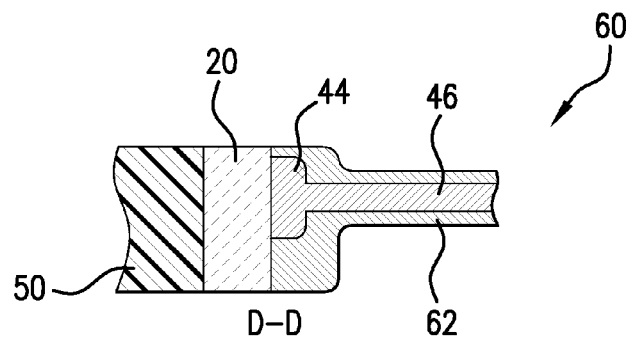
FIG. 21 is a side elevational sectional view of the objects of FIG. 16 at location D-D of FIG. 16.

This present invention constitutes a marked improvement in the field of electrosurgery, more particularly, to high efficiency electrosurgical surgical instruments and methods which use radio frequency (RF) electrical power and/or electrically heated filaments to destroy tumors, form lesions, denaturize, desiccate, coagulate and ablate soft tissues, as well as to drill, cut, resect and vaporize soft tissues.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention which will be limited only by the appended claims.

Elements of the Present Invention

In the context of the present invention, the following definitions apply:

The words "a", "an", and "the" as used herein mean "at least one" unless otherwise specifically indicated.

In common terminology and as used herein, the term "electrode" may refer to one or more components of an electrosurgical device (such as an active electrode or a return electrode) or to the entire device, as in an "ablator electrode" or "cutting electrode". Such electrosurgical devices are often interchangeably referred to herein as electrosurgical "probes" or "instruments".

The present invention makes reference to an "active electrode" or "active element". As used herein, the term "active electrode" refers to one or more conductive elements formed from any suitable metallic material, such as stainless steel, nickel, titanium, tungsten, and the like, connected, for example via cabling disposed within the elongated proximal portion of the instrument, to a power supply, for example, an externally disposed electrosurgical generator, and capable of generating an electric field.

The present invention makes reference to a "floating electrode" or "floating element". As used herein, the term "floating electrode" refers to one or more conductive elements formed from any suitable metallic material, such as stainless steel, nickel, titanium, tungsten, and the like, that, while disconnected from any power supply, is nevertheless but capable of intensifying the electric field in proximity to the active electrode and aid in bubble retention when the instrument is used to vaporize tissue.

The present invention makes reference to a "filament". As used herein, the term filament refers to one or more electrically powered conductive elements resistively heated to high temperatures.

The present invention makes reference to a "return electrode". As used herein, the term "return electrode" refers to one or more powered conductive elements formed from any suitable metallic material, such as stainless steel, nickel, titanium, tungsten, and the like, to which current flows after passing from the active electrode(s) and through the plasma field.

The term "proximal" refers to that end or portion which is situated closest to the user; in other words, the proximal end of an electrosurgical instrument of the instant invention will typically include the handle portion.

The term "distal" refers to that end or portion situated farthest away from the user; in other words, the distal end of an electrosurgical instrument of the instant invention will typically include the active electrode portion.

The present invention makes reference to the thermal treatment of tissue, more preferably soft tissue, even more preferably tumor tissue. As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. The present invention is not limited in terms of the tissue to be treated but rather has broad application to the thermal treatment of any target tissue with particular applicability to the ablation, removal and/or destruction of benign and cancerous tumors.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal.

Unless otherwise defined, all technical and scientific terms used herein have the same meaning as commonly understood by one of ordinary skill in the art to which this invention belongs. In case of conflict, the present specification, including definitions, will control.

Utilities of the Present Invention

As noted above, the present invention is directed to high efficiency monopolar or bipolar electrosurgical instruments and methods which utilize radio frequency (RF) energy, electrically energized filaments, and/or non-coherent radiation emitted by heated filaments to destroy tumors, form lesions, denaturize, desiccate, coagulate and ablate soft tissues, as well as to drill, cut, resect and vaporize soft tissues, with or without externally supplied liquids, having particular utility in the context of oncology, ear nose and throat (ENT), urology, gynecology, and laparoscopy, as well as general surgery.

Certain embodiments of the electrosurgical instrument of the present invention find particular utility in the treatment of tissue surfaces. Others are configured for sub-surface tissue treatment. Similarly, while some embodiments utilize the endogenous fluid of a "wet field" environment to transmit current to target sites, others require an exogenous irrigant. In certain embodiments, the irrigant is heated to the boiling point, whereby thermal tissue treatment arises through direct contact with either the boiling liquid itself or steam associated therewith.

As described in further detail below, in one aspect, the present invention expands on the floating electrode concept. For example, the present invention relates to the design and deployment of novel "floating electrode" electrosurgical instruments that use steam/hot fluid to thermally treat target tissue, both at the surface and below the surface.

A further aspect of the present invention involves the construction and use of hybrid monopolar/bipolar electrosurgical instruments that combine features of monopolar and bipolar instruments to concentrate the energy in the desired region of the tissue to be treated. More particularly, the present invention relates to the discovery of a new type of electrosurgical device, a hybrid between monopolar and bipolar instruments, that results in a novel electrosurgical therapeutic approach for the thermal treatment of tissue. Unlike a bipolar instrument, wherein the return electrode is mounted on the same shaft as the active electrode, according to the principles of this invention, the return electrode is not mounted on the same shaft. Unlike monopolar instruments, wherein the return electrode is mounted on the patient body far away from the surgical site, according to the principles of this invention, the return electrode may be mounted on the patient body close to the surgical site.

Such devices, according to the principles of the present invention, constitute hybrid instruments in the sense that the return electrode size, shape and location is playing a critically important, and beneficial role in distributing and focusing the RF current in the desired area. For illustration purposes of this concept, consider a case of treating a breast tumor. The return electrode may be externally attached to the skin of the patient breast being treated, and the instrument itself is inserted into the breast tissue/tumor, in close proximity to the return electrode. When energized, the RF energy is concentrated in the desired tissue/tumor region depending on the medical needs. More specifically, a specially designed return electrode (size, shape and position) and a specially designed active electrode(s) are used to optimize the energy distribution in the tissue over the desired area.

Usually the return (ground) electrode plays a "passive" role in electrosurgery in the sense that it does not effect the electrical energy distribution in the vicinity of the "active" electrode—the area where the tissue is being treated. This is a consequence of the return electrode being positioned too far away from the area being treated. In contrast, if the main active electrode is in close proximity of the surface of the body (skin), then positioning of a specially designed return electrode on the skin near area being treated can substantially and favorably effect the electrical energy distribution in the tissue. Moreover, the shape and position of return electrode can be changed during procedure for the purpose of optimizing the clinical effects. The devices may be used in conjunction with various fluids, bodily fluids or dry fields. This unexpected discovery provides a new modality, or a new method of electrosurgical therapeutic approach for the thermal treatment of tissue.

In a further aspect, the present invention relates to electrosurgical instruments that use hot filaments to generate plasma which may then be used to deliver energy for the thermal treatment of tissue. More particularly, the present invention relates to the discovery of a new type of plasma-based electrosurgical device that utilizes a hot filament (300-900° C.) to enhance plasma generation efficiency, ionization, arcing/sparking and effectiveness. In prior art plasma-based electrosurgical devices, like the argon beam coagulators mentioned above, a sufficiently high electrical voltage must be applied to the electrode, the voltage exceeding the breakdown threshold (electrical strength) of the gaseous gap, at which point an electrical breakdown (ionization) takes place forming plasma channels between the electrode and the tissue. The present invention utilizes a much more efficient approach to achieve gas ionization (plasma formation). In particular, the present invention uses schemes to substantially and permanently reduce the electrical breakdown threshold of the gaseous media between the electrode and the surface of the tissue. In this manner, the plasma can be generated efficiently at lower voltages (0.5-3 kV) than otherwise possible. According to the principles of this invention, this can be achieved, for example, by using a hot filament (electrode) to substantially reduce the electrical breakdown threshold of the gaseous gap between the electrode and the surface of the tissue. This result arises from the substantial enhancement of the probability of electron emission from the heated filament. The filament also enhances the intensity of the RF field in its vicinity, making it easier to maintain the plasma discharge. The heated filament also heats at least part of the discharge volume up to a high temperature and also seeds the discharge channel with ionized particles making it easier to support the discharge.

The instruments according to the principles of this invention may operate without gas flow, with a gas flow and with a reversed gas flow (gas suction). The instruments can operate in various fluids like liquid, gas or air or a combination of all the above at various pressures, including atmospheric pressure. The instruments according to the principles of this invention may operate in electrically conductive, such as saline, or non conductive fluids. Various embodiments are illustrated, as examples, in FIGS. 42 to 60, the details of which are discussed in further detail below. In all embodiments, a portion of the tissue surface can be coated with a thin layer of material with low potential of ionization. This material can be continuously evaporated to seed the discharge channel with neutral particles having low potential of ionization, again lowering the threshold for generating and maintaining the plasma channel. In this manner, the present invention provides a novel electrosurgical therapeutic approach for the thermal treatment of tissue, an approach that may be used in conjunction with various irrigants, fluids, and bodily fluids or, alternatively, in a dry environment.

In yet a further aspect, the present invention relates to the delivery of energy generated by an electrically heated filament to thermally treat target tissue. More particularly, the present invention relates to the discovery of a new type of minimally invasive instrument, based on miniature, intense sources of electromagnetic radiation in the form of non-coherent infra-red, visible and/or ultraviolet generated by an electrically heated filament mounted inside a disposable instrument. The instruments based on the principles of this invention can treat either large or small tissue areas, depending on the designs.

Specifically, in order to create a lesion close to an outer or an inner surface of tissue, the tissue has to be heated. The heating takes place if the tissue surface absorbs energy. The energy according to the principles of this invention is a non-coherent electromagnetic energy, such as infrared (IR), visible (V) and ultraviolet (UV) radiation, radiated by a filament heated to temperatures of approximately 500-2200° C. This radiation is absorbed by the surface of the tissue, heats the surface and adjacent layer of the tissue creating layer of surface lesion. The surface temperature rises as a function of time, tissue properties, area of absorption, radiation power, and distance between the filament and the tissue. By controlling the power of the source and distance to the surface of tissue, one can control the temperature of the layer of the tissue as well as the thickness of the lesion layer. Illustrative embodiments of such a device, using the above principles, are described in further detail below. In all embodiments, the source of radiation is an electrically heated open or encapsulated filament, heated to temperatures of approximately 500-2200° C., producing non-coherent IR, visible and UV radiation of enough power. The media between source and surface can be gaseous or liquid (conductive or non conductive), bodily fluids, solid or combination of above. Gas ventilation and liquid circulation, aspiration and irrigation may be used for cooling and/or removing byproducts and/or debris.

Figure 61:
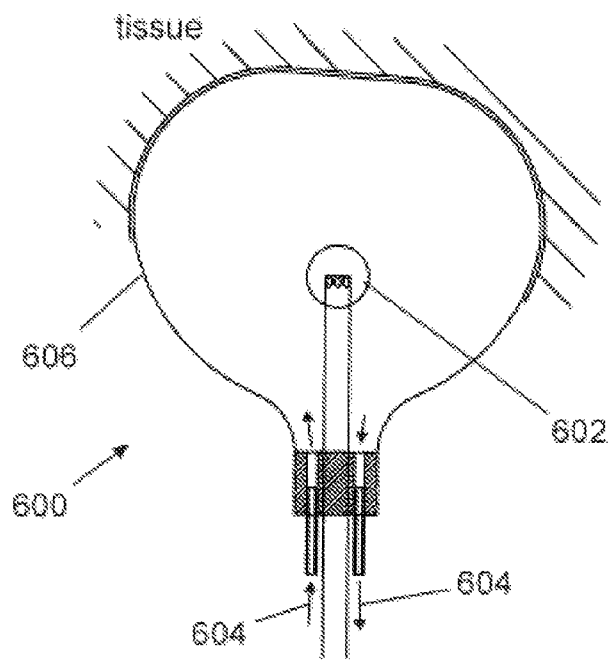
FIG. 61 is a schematic representation of an alternate embodiment for treating a cavity in a body using a miniature electromagnetic energy source.
Figure 62:
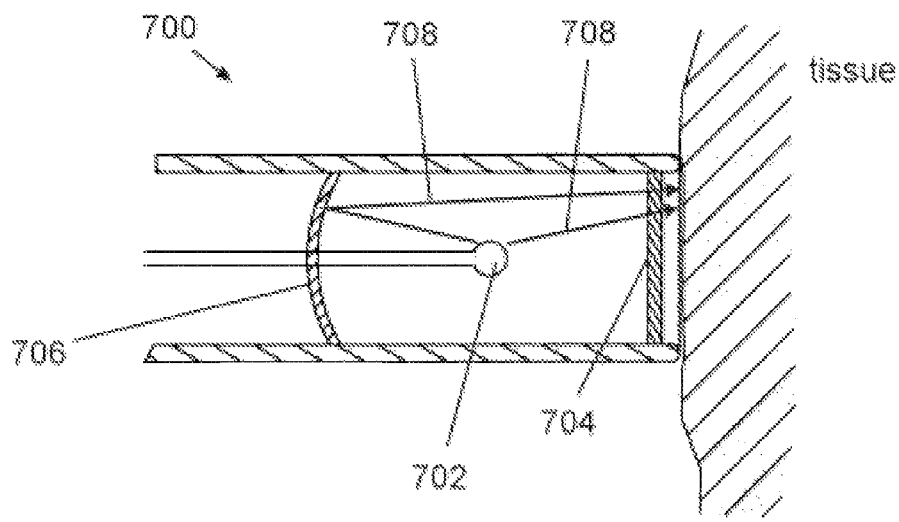
FIG. 62 is a schematic representation of an alternate embodiment for treating a surface using a miniature electromagnetic energy source.

As an example, two embodiments are illustrated in FIGS. 61 & 62, discussed in greater detail below. The embodiment shown in FIG. 61 includes an inflated transparent flexible bag with the heated filament source of non-coherent radiation inside, and also gas ventilation/circulation for cooling. The embodiment shown in FIG. 62 includes a directed movable energy source configured like a headlight (projector), with or without ventilation. However, many other embodiments may utilize the same principles of this invention. For example: (a) elongated miniature linear versions (b), encapsulated or non-encapsulated heated filament for insertion directly into tissue; (c) Filament/heater coated with an insulator; (d) an external filament/energy source coupled via a fiber optic to bring the energy into the desired area to be treated; (e) same of the above with channels in insulators for additional driving of RF current, monopolar and/or bipolar; (f) various geometries of the above instrument, like cylindrical, linear, spherical, curvilinear, polygonal and or combinations of the above; (g) embodiments can include a flexible bag with controlled transparency and gas ventilation for cooling; (h) miniature versions and combinations of the above. Thus, the present invention provides a new therapeutic approach for thermal tissue treatment, a method that may be used in conjunction with various fluids, bodily fluids or dry fields.

The tissue treatment instruments of the present invention may be used in conjunction with existing diagnostic and imaging technologies, for example imaging systems including, but not limited to, MRI, CT, PET, x-ray, fluoroscopic, and ultrasound. Such imaging technology may be used to monitor the introduction and operation of the instruments of the present invention. For example, existing imaging systems may be used to determine location of target tissue, to confirm accuracy of instrument positioning, to assess the degree of thermal tissue treatment (e.g., sufficiency of tissue removal), to determine if subsequent procedures are required, and to assist in the atraumatic removal of the instrument.

As noted above, the instruments of the present invention find utility in thermal tissue treatment, more particularly in thermal treatment of tumor tissue, both benign and cancerous, to destroy tumors, form lesions, denaturize, desiccate, coagulate and/or ablate tumor tissues, as well as to drill, cut, resect and vaporize tumor tissues, with or without externally supplied liquids. Though the present invention is not particularly limited to the treatment of any one specific disease or the removal of any one specific type of tumor, the instruments of the present invention nevertheless find particular utility in the treatment and removal of liver, breast, bladder and spinal tumors, uterine fibroids, ovarian cysts, and colon polyps as well as the treatment of noncancerous conditions such as endometriosis.

Illustrative Embodiments of the Present Invention

Hereinafter, the present invention is described in more detail by reference to the exemplary embodiments. However, the following examples only illustrate aspects of the invention and in no way are intended to limit the scope of the present invention. As such, embodiments similar or equivalent to those described herein can be used in the practice or testing of the present invention.

Referring to FIGS. 1 through 6, which depict an insulator of an electrosurgical instrument of the present invention that is particularly suited to thermally treating patient tissue, insulator 20 has a distal end portion 22, a proximal end portion 24 and mid-portions 26. Distal end portion 22 has formed in its proximal face cylindrical recesses 28. Proximal end portion 24 has axial cylindrical openings 30 axially aligned with recesses 28. Mid-portions 26 have formed in lower surface 32 channels 34. Insulator 20 is made from a suitable dielectric material, examples of which include, but are not limited to, alumina, zirconia, and high-temperature polymers.

Referring to FIG. 7 through 10, which depict an active electrode of an electrosurgical instrument of the present invention that is particularly suited to thermally treating patient tissue, active electrode 40 has a distal portion forming parallel cylindrical portions 42 connected by flange 44 to proximal conductor 46. Electrode 40 may be formed from any suitable metallic material, examples of which include, but are not limited to, stainless steel, nickel, titanium, tungsten, and the like.

FIGS. 11 through 15 depict a floating electrode for an electrosurgical instrument of the present invention that is particularly suited to thermally treating patient tissue. As shown herein, the floating electrode 50 forms adjacent channels having a common flange 52, and lateral flanges 54 and wall 56. Flanges 52 and 54 have ends 58 formed to a radius. However, the present invention is not limited to the depicted design and includes alternate floating electrode embodiments, such as those described in co-pending U.S. patent application Ser. Nos. 10/911,309 (published as US 2005-0065510) and 11/136,514 (published as US 2005-023446) cited above, the contents of which are incorporated by reference herein in their entirety. Referring now to FIGS. 16 to 21, which depict a distal portion of an electrosurgical instrument of the present invention formed from the components of FIGS. 1 through 15, the distal portion of probe 60 is an assembly in which distal portions 42 of active electrode 40 are positioned within channel portions 34 of insulator 30. Floating electrode 50 is positioned between distal portion 22 and proximal portion 24 of insulator 20. Dielectric coating 62 covers flange 44 and conductor 46 of active electrode 40. Conductor 40 is connected by means within the probe 60 and electrical cable to a suitable electrosurgical generator.

Figure 22:
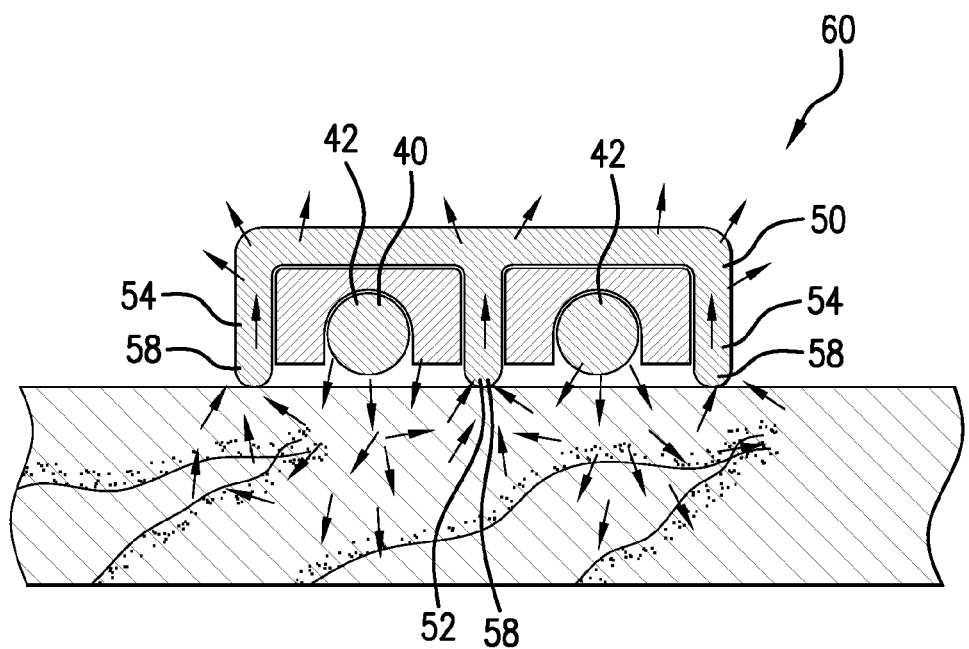
FIG. 22 is an axial sectional view of the objects of FIG. 16 during use showing current flow.
Figures 23, 26:
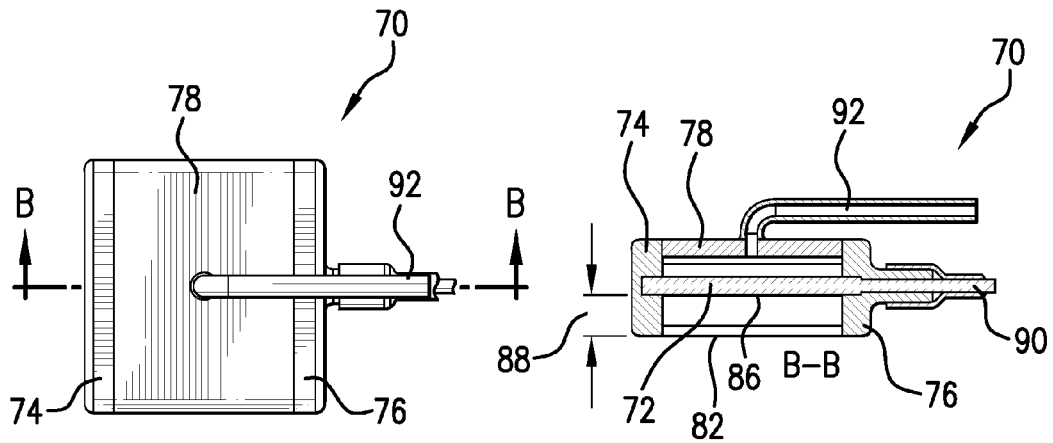
FIG. 23 is a plan view of a distal portion of an alternate embodiment electrosurgical instrument adapted for thermal tissue treatment near a tissue surface.
FIG. 26 is a side elevational sectional view of the objects of FIG. 23 at location B-B of FIG. 23.
Figures 24, 27:
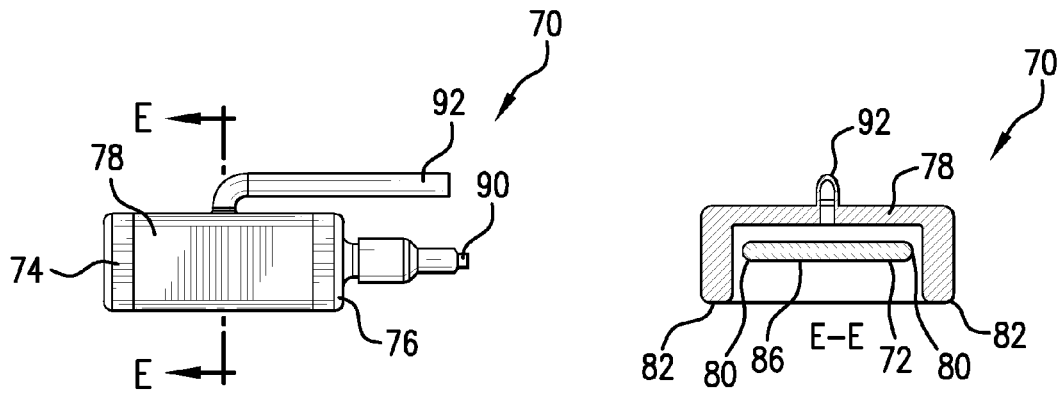
FIG. 24 is a side elevational view of the objects of FIG. 23.
FIG. 27 is an axial sectional view of the objects of FIG. 23 at location E-E of FIG. 24.
Figure 25:
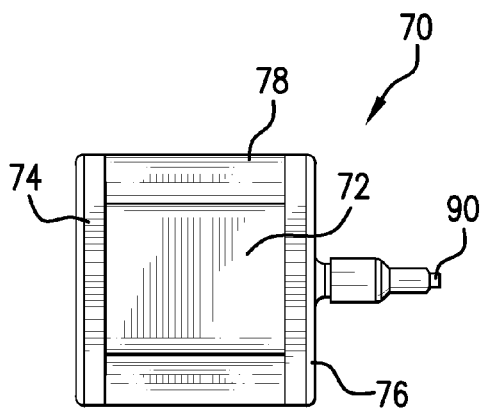
FIG. 25 is a bottom side plan view of the objects of FIG. 23.

FIG. 22 depicts probe 60 in use, fully or partially submerged in irrigant (either endogenous to site or exogenously supplied). Flanges 52 and 54 of floating electrode 50 contact the tissue. Distal portions 42 of active electrode 40 may contact the tissue, or may contact the fluid in a gap between the electrode 40 and the tissue. Fluid surrounding the distal end of probe 60 is conductive. It may be supplied to the site as a conductive liquid such as standard saline, or may be supplied to the site as a non-conductive irrigant such as water, the fluid becoming conductive by contamination by body fluids such as blood, or by ablation by-products.

During use, current (indicated by arrows) flows from active electrode 40 to a return electrode (not shown), either at a remote site or mounted on the instrument 60. Current flows from distal portions 42 of active electrode 40 through tissue in contact with or in close proximity to portions 42. Some current flows through the tissue to the return electrode. A portion of the current flows through the tissue to radiused portions 58 of flanges 52 and 54 of floating electrode 50 in contact with the tissue to portions of floating electrode 50 in lower potential portions of the electric field. This current then flows from floating electrode 50 to conductive fluid in contact therewith, and then through the fluid to the return electrode. The efficiency of probe 60 for thermally treating tissue is enhanced by the elimination of regions of high current density. Such regions of high current density cause boiling of irrigant in close proximity, and arcing through the steam bubbles formed so as to vaporize tissue. The absence of these regions allows the device to be used at higher power levels for more rapid tissue treatment without creating these undesirable vaporizing sparks. Specifically, portions of flanges 52 and 54 which contact tissue are radiused so as to eliminate sharp corners which create regions of high current density. In addition, portions 42 of active electrode 40 are also rounded to eliminate sharp edges which create regions of high current density.

FIGS. 23 through 27 depict the distal portion of another thermal treatment electrosurgical instrument of the present invention. Probe 70 has a planar active electrode 72 suspended by distal dielectric end piece 74 and proximal dielectric end piece 76 in an inverted channel formed by floating electrode 78. Lateral edges 80 of active electrode 72, and edges 82 of floating electrode 78 are radiused. Lower surface 86 of active electrode 72 is recessed distance 88 from the plane of edges 82 of floating electrode 78. Conductor means 90 within probe 70 and cabling connect active electrode 72 to a suitable electrosurgical generator. Tubular member 92 is connected by means within probe 70 to an external conductive irrigant source.

Although the active electrode assembly is depicted as a having a square/rectangular profile and/or cross-section, the invention is not limited to the depicted configuration. So long as a particular configuration provides the requisite confined space, more particularly the presence of a fluid-fillable cavity defined between the active and floating electrodes, other geometries may be contemplated including, but not limited to, electrode assemblies having rounded, circular, elliptical, and polygonal profiles.

Figure 28:
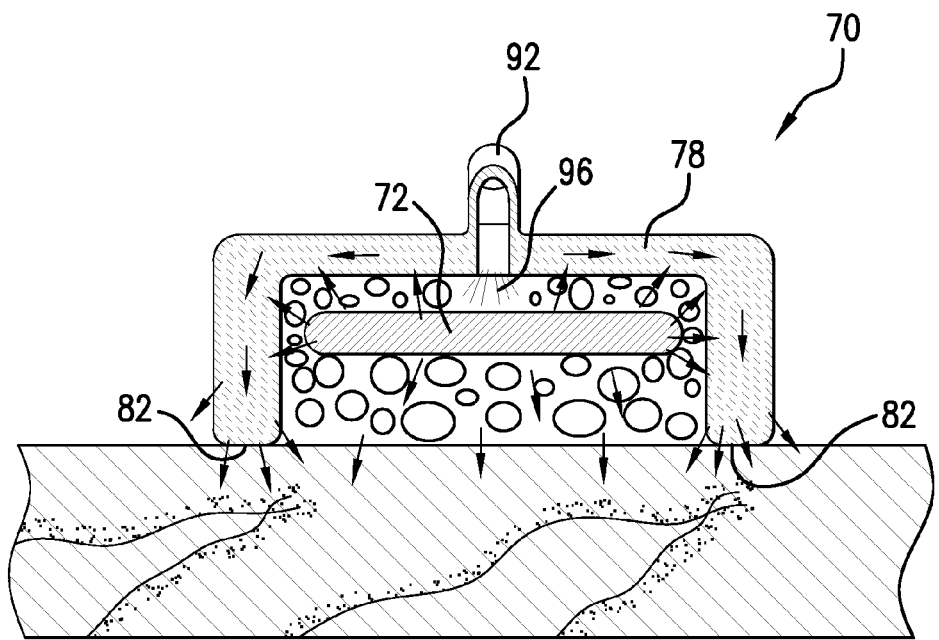
FIG. 28 is an axial sectional view of the objects of FIG. 23 in use in a dry field environment.

Referring now to FIG. 28, which depicts probe 70 in use in a "dry field", conductive irrigant 96 may be supplied by tubular member 92 to the interior of the distal portion of probe 70, between the upper surface of active electrode 72 and the interior surface of floating electrode 78. Current (indicated by arrows) flows from active electrode 72 to a return electrode, either remotely located or on probe 70. A portion of the current flows through conductive liquid surrounding active electrode 72 to floating electrode 78 and therethrough to tissue in contact with or close proximity to edges 82. Current flowing from the floating electrode 78 to the tissue in this manner is conducted through direct contact or through conductive fluid in close proximity. A second portion of the current flows from the active electrode 72 to the tissue through conductive fluid between active electrode 72 and the tissue. Current flowing through conductive irrigant 96 heats irrigant 96 primarily in the regions in which active electrode 72 and floating electrode 78 are in close proximity. If the current flow is sufficiently high related to the flow rate of conductive irrigant 96, boiling of irrigant 96 occurs. Expanding steam and irrigant flow from tubular member 92 causes heated liquid and steam to flow into the region between active electrode 72 and the tissue. Thermal treatment of the tissue is accomplished through contact with heated liquid and steam, and through flow of current. The relative proportion of the two depends on the power supplied and the flow rate of conductive irrigant 96.

Figure 29:
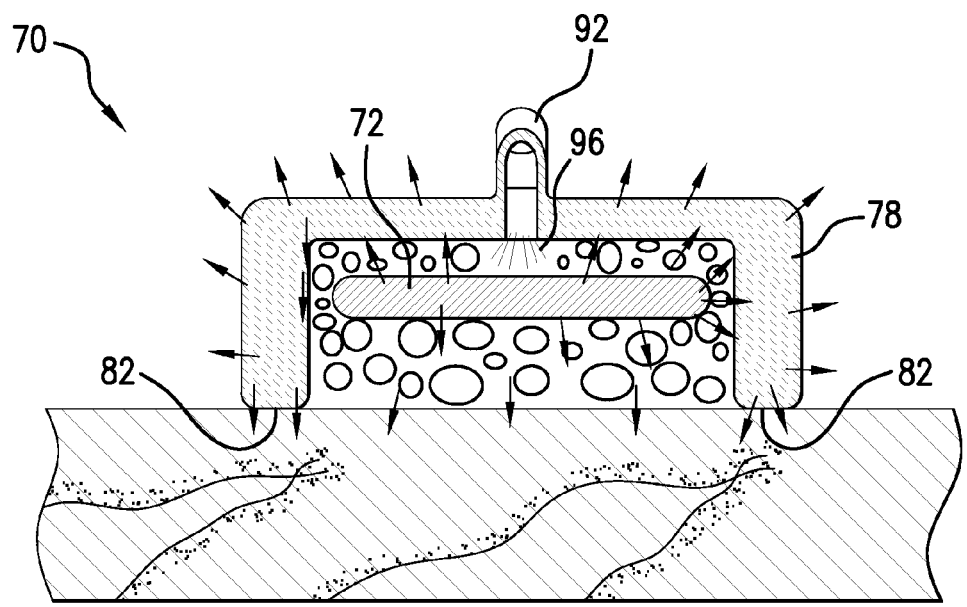
FIG. 29 is an axial sectional view of the objects of FIG. 23 in use in a conductive fluid environment.

FIG. 29 depicts probe 70 in use in a conductive liquid environment. Conductive irrigant 96 is supplied by tubular member 92 to the interior of the distal portion of probe 70, between the upper surface of active electrode 72 and the interior surface of floating electrode 78. Current flows from active electrode 72 to a return electrode, either remotely located or on probe 70. A portion of the current flows through conductive liquid surrounding active electrode 72 to floating electrode 78 and therethrough to conductive liquid in contact with the exterior surfaces of floating electrode 78. A second portion of the current flows from the active electrode 72 to the tissue through conductive fluid between active electrode 72 and the tissue. Current flowing through conductive irrigant 96 heats irrigant 96 primarily in the regions in which active electrode 72 and floating electrode 78 are in close proximity. If the current flow is sufficiently high related to the flow rate of conductive irrigant 96, boiling of irrigant 96 occurs. Expanding steam and irrigant flow from tubular member 92 causes heated liquid and steam to flow into the region between active electrode 72 and the target tissue. Thermal treatment of the tissue is accomplished through contact with heated liquid and steam, and through flow of current. The relative proportion of the two depends on the power supplied and the flow rate of conductive irrigant 96. As with the instrument 60 previously herein described, probe 70 is designed to minimize or eliminate regions of high current density which cause arcing and tissue vaporization. Particularly, edges 82 of floating electrode 78 which contact target tissue are rounded to eliminate regions of high current density and arcing which may result therefrom. Also, lateral edges 80 of active electrode 72 are radiused to prevent arcing between active electrode 72 and the tissue or between electrode 72 and floating electrode 78. Lower surface 86 of active electrode 72 does not have features such as grooves, protuberances, recesses which increase current density, but is smooth. These features, individually and/or in combination, allow probe 70 to be used at higher power levels for more rapid tissue treatment without arcing and the resulting undesirable tissue vaporization.

Figure 30:
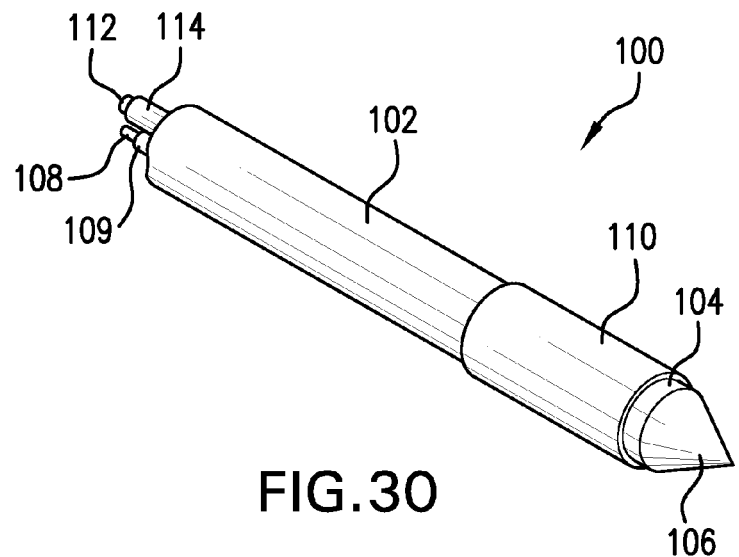
FIG. 30 is a perspective view of a distal portion of an alternate embodiment RF electrosurgical instrument adapted for thermal tissue treatment at a location remote from the tissue surface (e.g., sub-surface).
Figure 31:
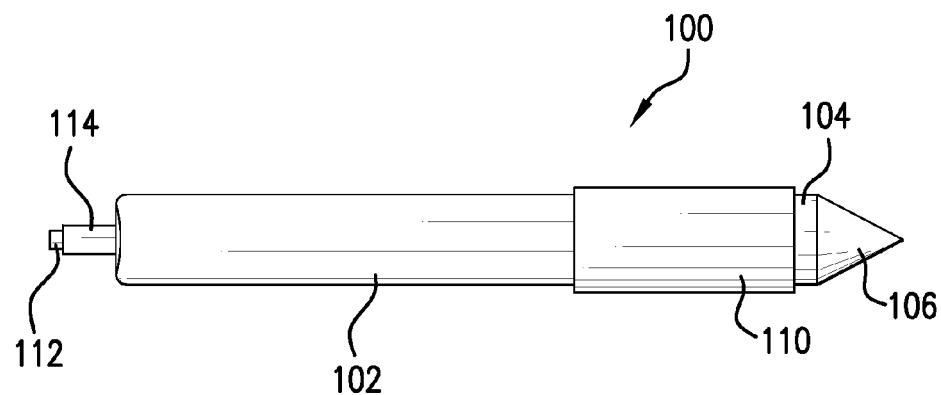
FIG. 31 is a plan view of the objects of FIG. 30.
Figure 32:
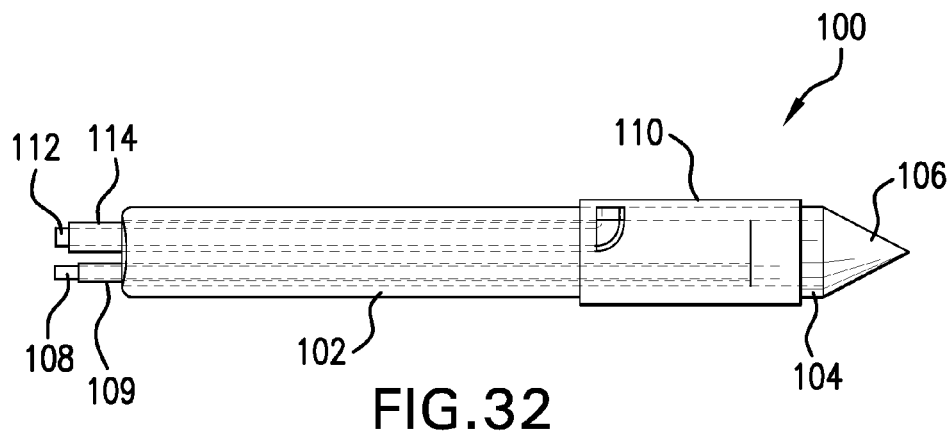
FIG. 32 is a side elevational sectional view of the objects of FIG. 30 at location A-A of FIG. 31.

FIGS. 30 through 32 depict the distal portion of an electrosurgical instrument of the present invention that is particularly suited to the thermal treatment of tissue, more particularly sub-surface tissue treatment. While the previous embodiments are designed for surface treatment, electrosurgical instrument 100 thermally treats tissue into which it is inserted. Probe 100 is formed from a dielectric tube 102 having a sharpened, tapered or conical distal end 104 that facilitates atraumatic insertion into the target tissue. To distal end 104 is mounted active electrode 106 connected by conductor 108 insulated by dielectric coating 109 and means within probe 100 and cabling to a suitable electrosurgical generator. Tubular conductive member 110 is assembled to dielectric tube 102 near its distal end, and connected by conductor 112 insulated with dielectric coating 114 to a control element in the handle portion of probe 100. The control element has a first position in which conductor 112 is not connected to the electrosurgical generator, and a second position in which the conductor 112 is connected to the generator output such that when the generator is activated RF voltage is applied to member 110.

During use, probe 100, while energized, is first inserted into the tissue, tubular member 110 functioning as a floating electrode, the switching means being in its first position. When probe 100 is inserted to the desired depth, switching means is put in its second position and RF energy is supplied to conductive member 110 so as to treat tissue in close proximity.

Figure 33:
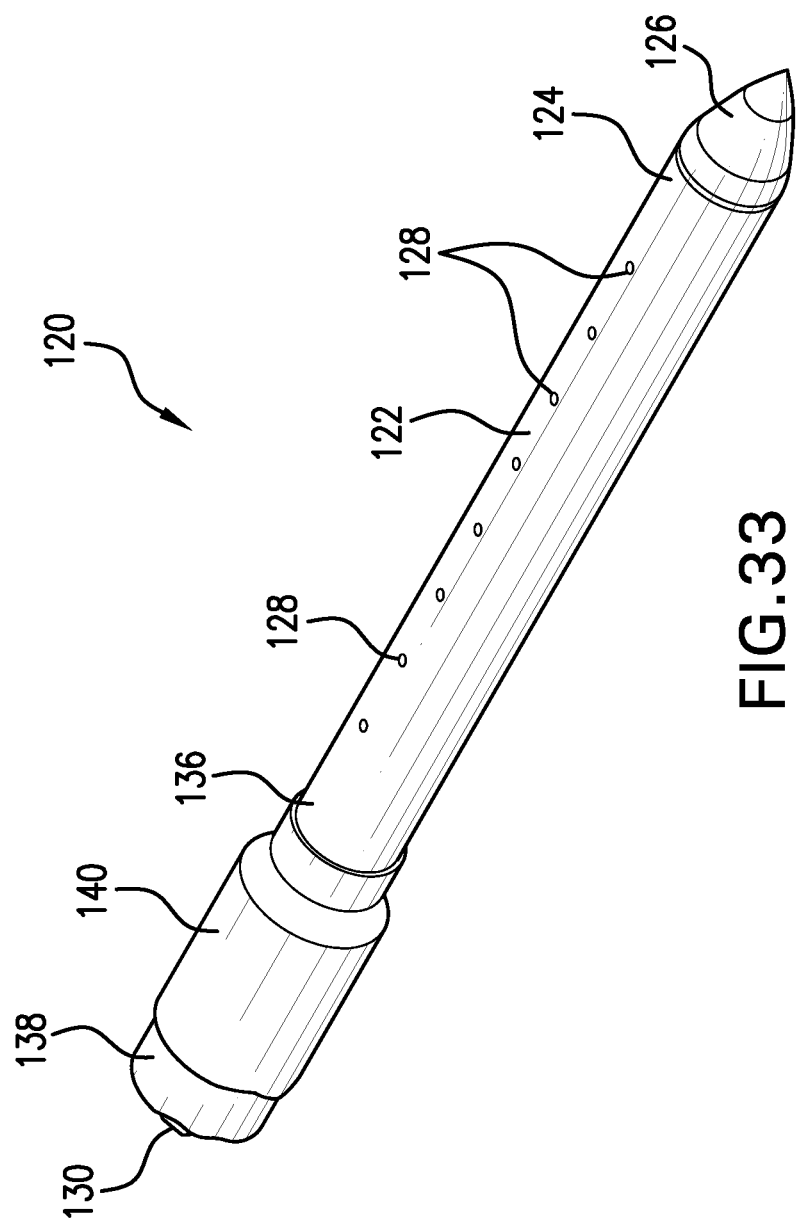
FIG. 33 is a perspective view of a distal portion of an alternate embodiment RF electrosurgical instrument adapted for thermal tissue treatment at a location remote from the tissue surface (e.g., sub-surface).

FIGS. 33 through 35 depict another embodiment of an electrosurgical instrument of the present invention that is particularly suited to thermal treatment of tissue into which it is inserted. Probe 120, the distal portion of which is shown has a first conductive tubular member 122 having a distal end 124 in which is mounted dielectric member 126. Member 122 has a plurality of ports or perforations 128. Second tubular member 130 is coaxially positioned within member 122, and has a distal end 132 positioned within a recess in dielectric member 126. Second tubular member 130 with lumen 133 has a plurality of perforations 134. Proximal end 136 of member 122 is mounted to tubular member 138, the distal end of first tubular member 138 and proximal portion of member 122 are covered by dielectric coating 140. Second tubular member 130 is connected by means within probe 120 and cabling to a suitable electrosurgical generator. Region 142 is defined by the interior surface of first tubular member 122 and the exterior surface of second tubular member 130. Second tubular member 130 is connected by means within probe 120 and tubing to an external source for conductive irrigant.

Figure 36:
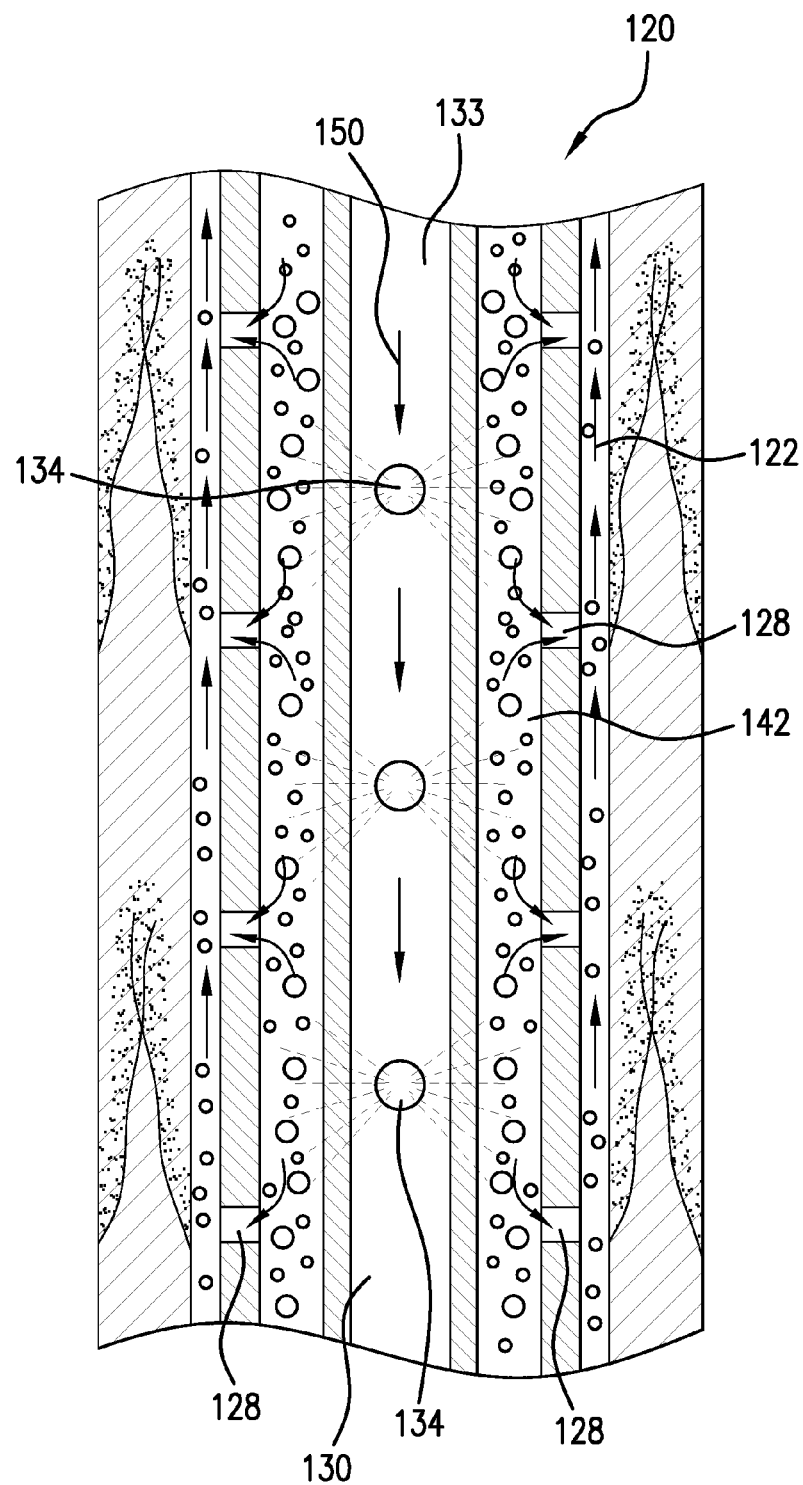
FIG. 36 is a sectional view of the objects of FIG. 33 during use.

Referring now to FIG. 36 depicting a portion of probe 120 during use, probe 120 is inserted into tissue to be thermally treated. Conductive irrigant 150 is supplied to lumen 133 of second tubular member 130. Lumen 133, perforations 134, region 142, and perforations 128 together form a flow path for irrigant 150 from lumen 133 of second tubular member 130 to region 144 between the external surface of probe 120 and the tissue into which it is inserted. Current flows from second tubular member 132 which acts as an active electrode, through conductive irrigant 150 to first tubular member 122, and therethrough to adjacent tissue via conductive irrigant in the gap between probe 120 and the tissue, and finally to a return electrode (not shown), either remotely located or on probe 120. First tubular member 122 is not connected to the electrosurgical unit, but has a floating potential between that of the active electrode (second tubular member 130) and the tissue. Current flowing through irrigant 150 in region 142 heats the irrigant causing it to boil. Irrigant 150 flowing from region 142 through perforations 128 is a two-phase mixture of steam and liquid which heats tissue with which it is in contact. The relative portions of steam and liquid are determined by the flow rate of irrigant 150, and by the applied power level. Decreasing the power or increasing the flow rate will cause the liquid phase to increase. Tissue thermally treated by probe 120 is heated by the irrigant and by resistive heating caused by current flow. The RF energy supplied to probe 120 has characteristics selected to minimize arcing within bubbles in the irrigant, and between member 122 and adjacent tissue.

Figure 37:
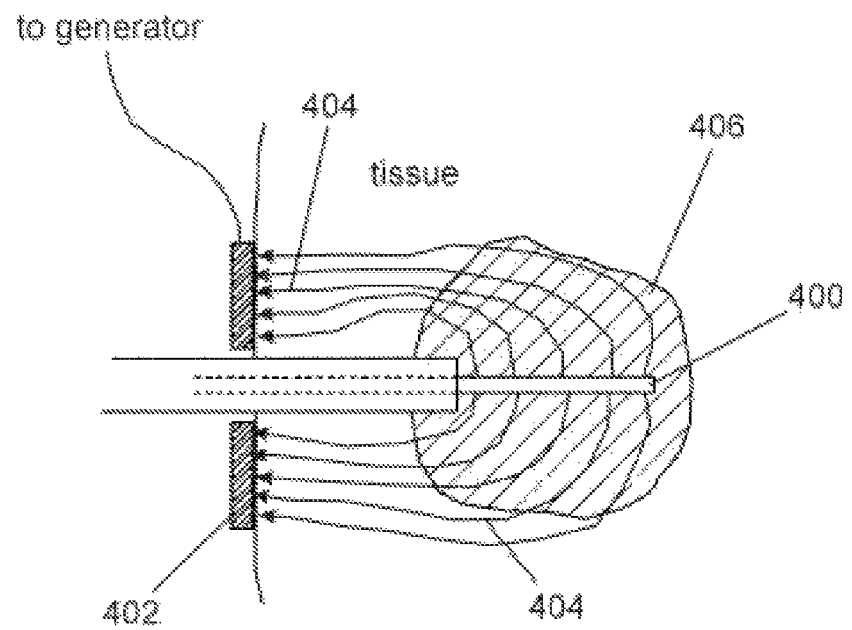
FIG. 37 is a side elevational view of the distal portion of an alternate embodiment.

FIG. 37 is an illustrative example of the above-described hybrid electrosurgical instrument of the present invention. In particular, the instrument of FIG. 37 includes an active electrode 400 which is embedded in the tumor 406 and a return electrode 402 on the instrument which contacts a free surface of the tissue near the tumor so as to concentrate the current flow 404 between the active and return electrodes, through the tumor.

Figure 38:
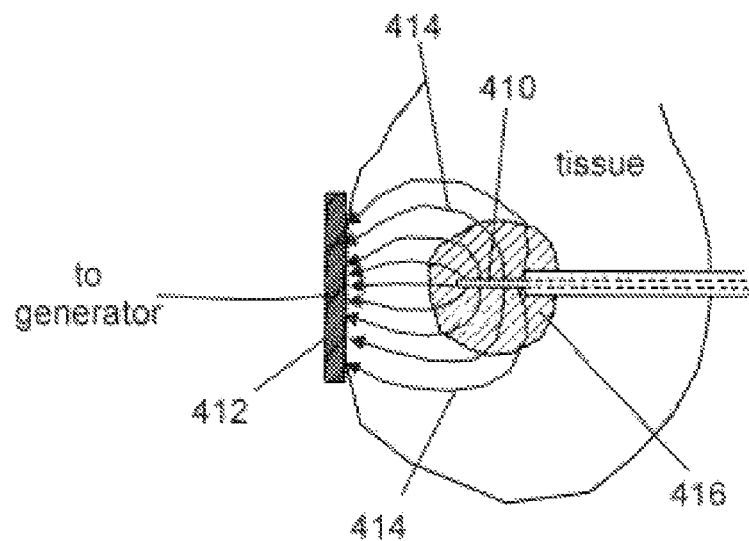
FIG. 38 is a side elevational view of the distal portion of an alternate embodiment.

An alternate embodiment of the above-described hybrid electrosurgical instrument of the present invention is depicted in FIG. 38. The instrument of FIG. 38 includes an active electrode 410 which is embedded in the tumor 416 and a return electrode 412 not on the instrument which contacts a free surface of the tissue near the tumor so as to concentrate the current flow 414 between the active 410 and return electrodes 412, through the tumor.

Figure 39:
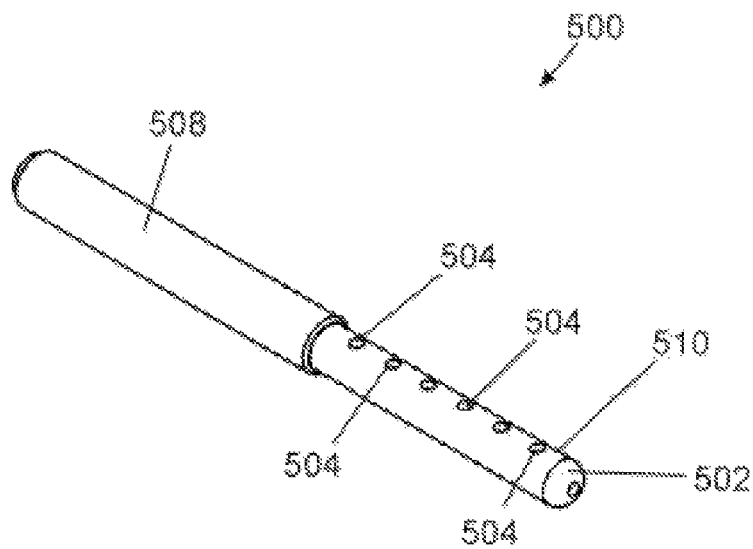
FIG. 39 is a perspective view of the distal portion of an alternate embodiment.
Figure 40:
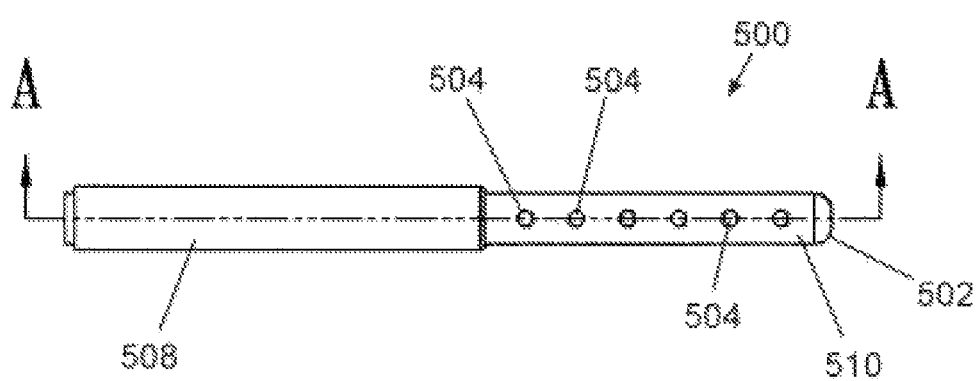
FIG. 40 is a plan view of the objects of FIG. 38
Figure 41:
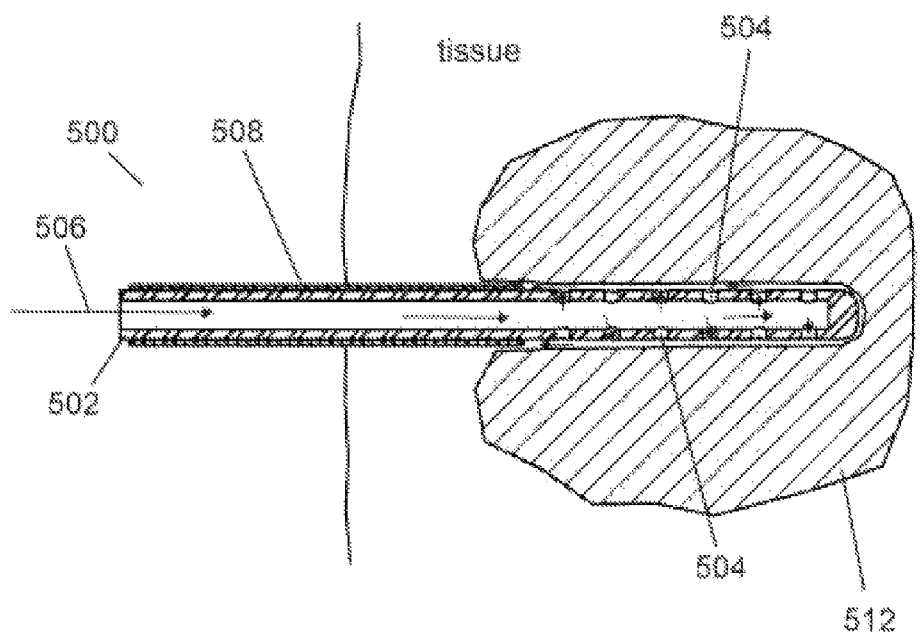
FIG. 41 is a side elevational sectional view of the objects of FIG. 38 at location A-A of FIG. 39 during use.

FIGS. 39 through 41 depict the distal portion 500 of an alternate embodiment designed to be embedded in a tumor 512 to go undergo treatment, the probe having a tubular active electrode 502 covered by dielectric coating 508 except for uninsulated portion 510 with perforations 504 such that irrigant 506 supplied to the active electrode flows from the electrode through perforations 504 so as to prevent desiccation and burning of tissue in contact with the electrode. In an alternate embodiment also designed to be embedded in a tumor to go undergo treatment, the probe distal portion construction is identical to that of distal portion 500, with the exception that uninsulated portion 510 of active electrode 502 is formed from a porous metallic material and perforations 504 are eliminated. Irrigant supplied to the active electrode flows from the electrode 502 through the porous material so as to prevent desiccation and burning of tissue in contact with the electrode. In yet another embodiment, perforations 504 are eliminated, and irrigant is supplied to the site by an annular passage between active electrode 502 and dielectric coating 508. As with the previous embodiments, irrigant so supplied prevents desiccation and burning of tissue in contact with the electrode.

Most widely used electro surgical electrodes—ablators, coagulators, evaporators, cutters, electrodes for lesion forming and electrodes for treatment of tumors (often referred to as tumor ablation) need to be very close to or in direct contact with the tissue being treated in order to be effective. Electrosurgical instruments like the Argon Beam Coagulator (Conmed Corporation, Utica, N.Y.) and other similar devices operate without direct contact with the tissue. These instruments employ a gaseous gap between the instrument's electrode and the tissue. The electrode is insulated, and high voltage is applied to the gaseous gap between electrode and the surface of the tissue. If sufficiently high voltage is applied to the electrode, the electric field exceeds the breakdown threshold (electrical strength) of the gaseous gap, and electrical breakdown takes place forming a plasma channel between the electrode and the tissue. This electrically conductive plasma channel acts as a non-contact extension of the electrode, allowing treatment at a "stand-off" distance. Instruments based on this scheme, sometimes referred to as plasma torches, generally require very high voltages (up to 10-20 kV), which are beyond the capability of standard, general purpose, commonly available electrosurgical radio-frequency (RF) generators. In addition, plasma torches require specially shaped electrodes, a flow of gas (usually a noble gas jet), a specially designed nozzle to control the gas flow, and high voltage circuitry to bring high voltage to the proximity of the surgical field.

Advanced, non-contact, plasma-based electrosurgical instruments constructed in accordance with the principles of this invention may be operated in the plasma torch regime yet are compatible with "standard" electrosurgical RF generators. The electrosurgical instruments of the present invention (which may be single-use disposables) can operate without a gas flow, with a gas flow and with a reversed gas flow (gas suction). The electrosurgical instruments of the present invention substantially and permanently reduce the electrical breakdown threshold of the gaseous gap between the electrode and the surface of the tissue. In addition, the plasma can be generated efficiently at low voltages (0.5-2 kV), thereby allowing for the use of general purpose, standard electrosurgical RF generators. Among the factors employed to achieve this goal are increasing the probability of electron emission from electrode; heating at least part of the discharge volume; seeding the discharge channel with ionized particles; filling the discharge channel with gas having a low rate of attraction of electrons; and seeding the discharge channel with neutral particles with low potential of ionization.

Figure 42:
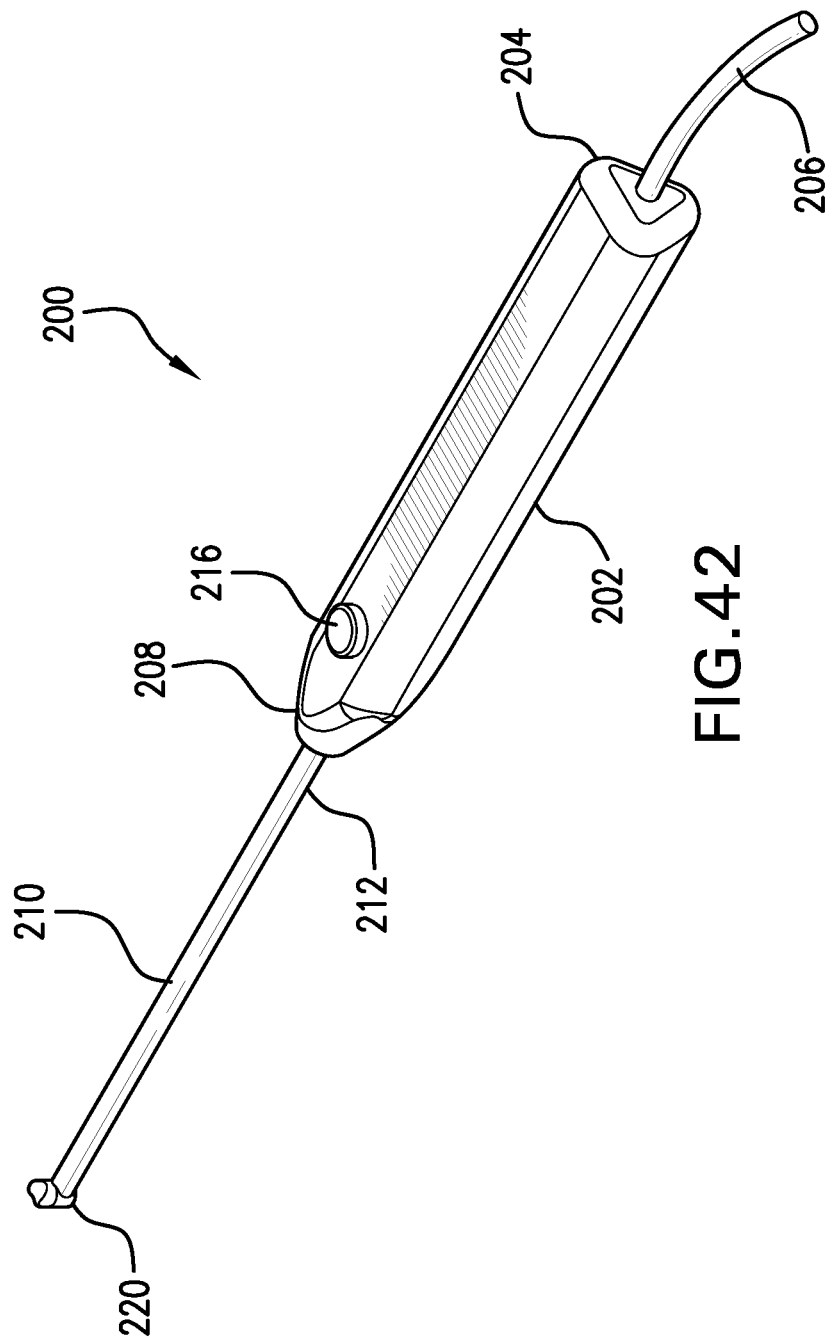
FIG. 42 is a perspective view of an alternate embodiment probe.
Figure 45:
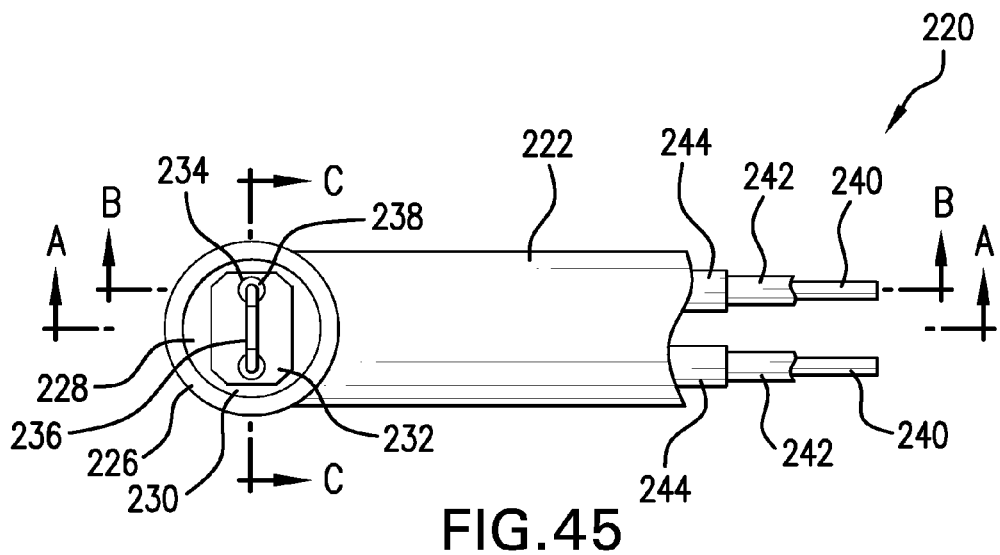
FIG. 45 is an expanded view of the distal portion of the instrument of FIG. 42.
Figure 46:
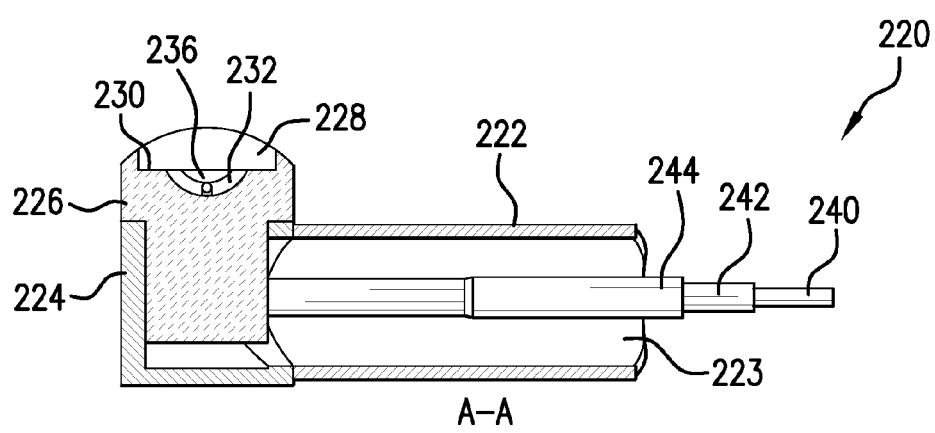
FIG. 46 is a side elevational sectional view of the objects of FIG. 44 at location A-A of FIG. 45.
Figure 47:
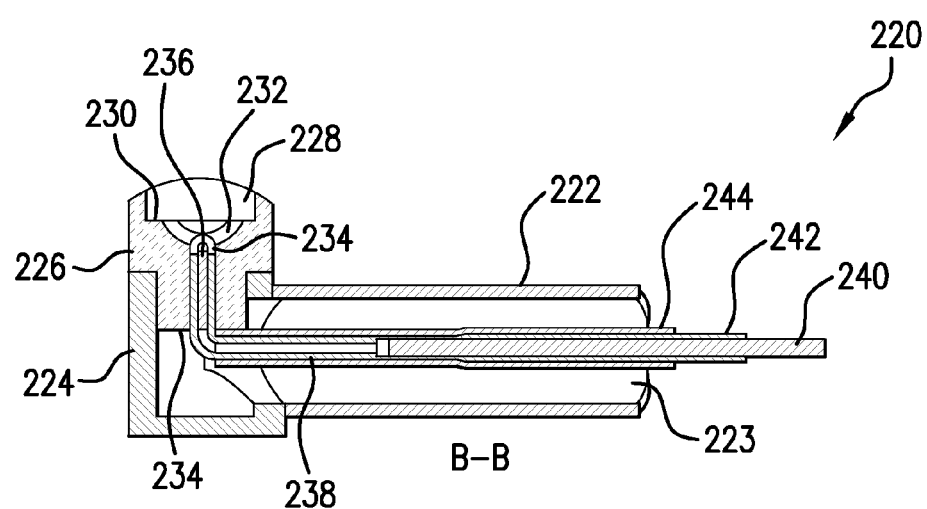
FIG. 47 is a side elevational sectional view of the objects of FIG. 44 at location B-B of FIG. 45.
Figure 48:
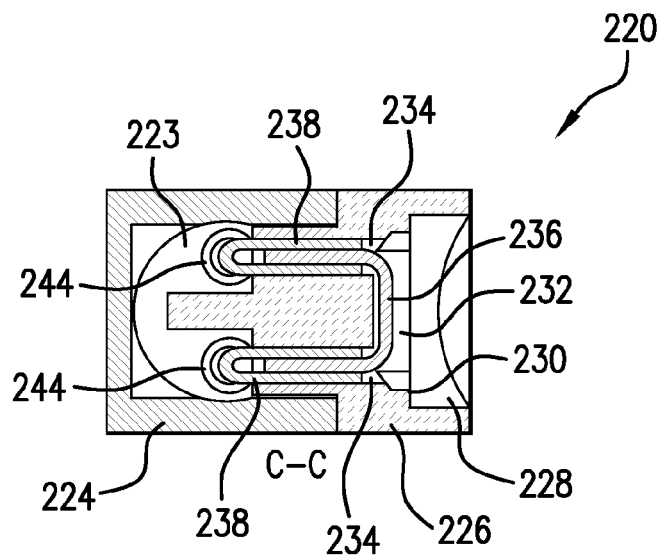
FIG. 48 is an axial sectional view of the objects of FIG. 44 at location C-C of FIG. 45.
Figure 49:
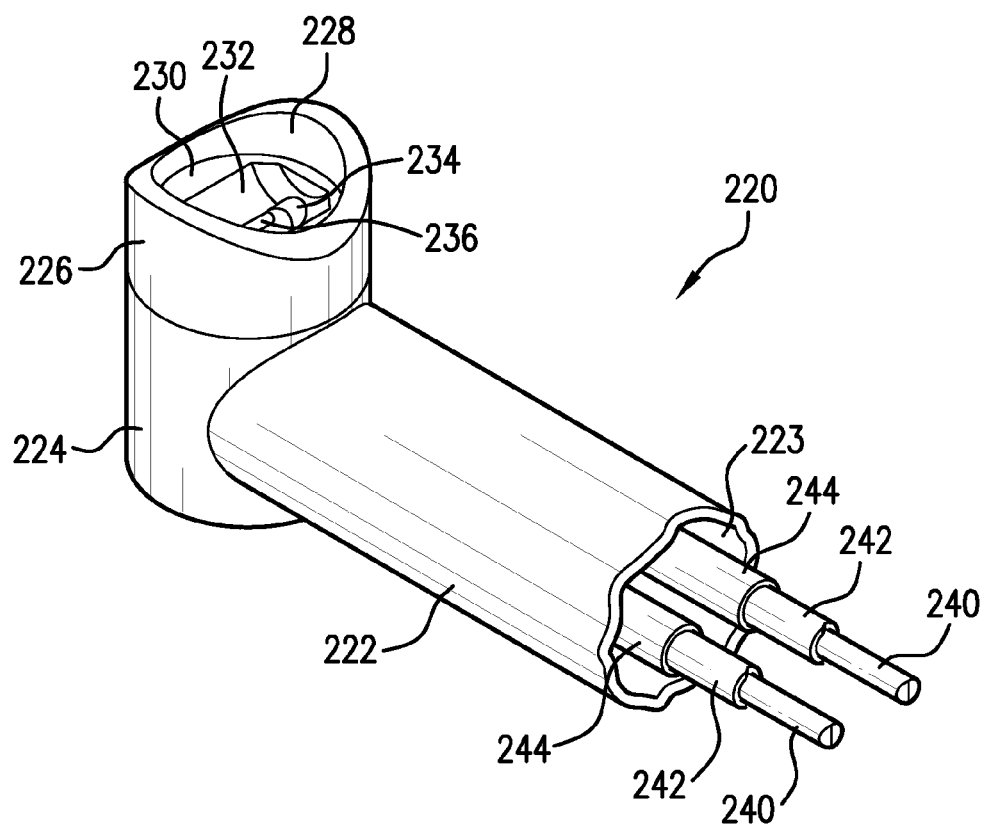
FIG. 49 is a perspective view of the objects of FIG. 45.

Referring now to FIGS. 42 through 44 which depict an embodiment of an electrosurgical instrument of the present invention that utilizes a hot filament to generate plasma channel particularly suited to the thermal treatment of surfaces, probe 200 has a proximal portion 202 forming a handle having a proximal end 204 from which passes electrical cable 206 which is connected to a suitable electrosurgical generator, and a distal end 208 from which protrudes elongated instrument distal portion 210. Portion 210 has a proximal end 212 mounted to handle portion 202, and a distal end 220. Activation button 216 controls the electrosurgical generator to which probe 200 is connected by cable 206. Handle portion 202 contains batteries 218.

Referring now to FIGS. 45 through 49 depicting the active distal end of 220 of distal portion 210 of probe 200, elongated tubular member 222 with lumen 223 has mounted to its distal end closed-end tubular member 224 to which is mounted insulator 226. Insulator 226 has a first recess 228 formed coaxial with insulator 226, recess 228 having a planar surface 230. Surface 230 has formed therein second recess 232. Insulator 226 has formed therein passages 234 between second recess 232 and surface 234 of insulator 226. Filament wire 236 is connected to tubular members 238 to wires 240 in lumen 223 of tubular member 222, wires 240 being connected by circuitry within handle portion 202 to batteries 218, and by cable 206 to the electrosurgical generator such that depressing activation button 216 causes batteries 218 to supply the battery voltage to filament 236, and the electrosurgical generator to supply RF voltage to filament 236. Insulation 242 covers wires 240. Insulation 244 covers the proximal portion of tubular members 238, and the distal portion of wires 240.

Figure 50:
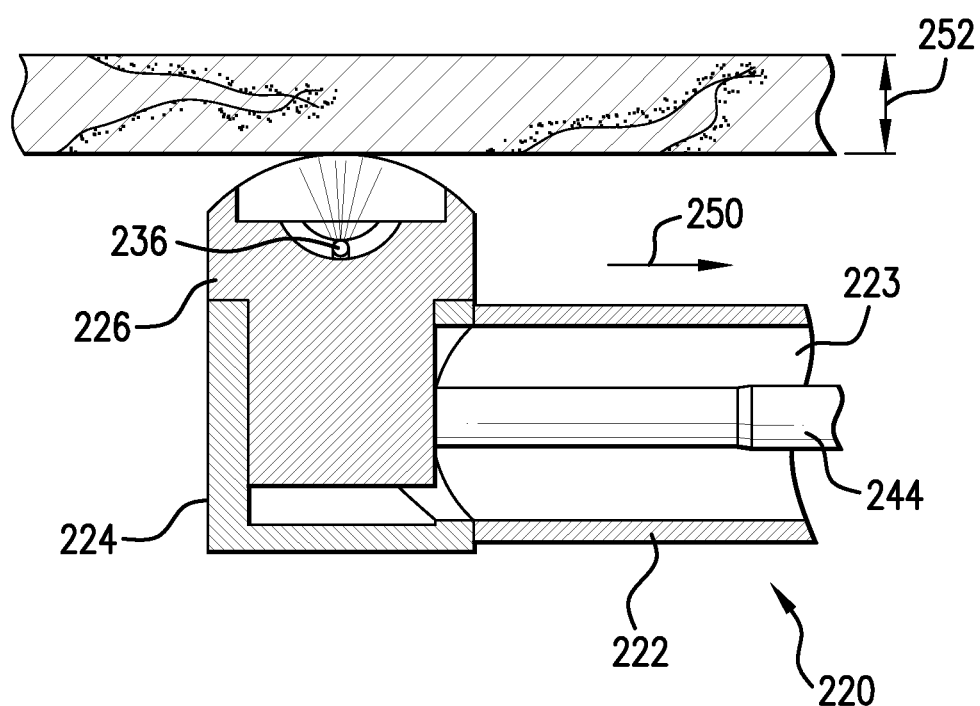
FIG. 50 is a side elevational sectional view of the distal portion of the instrument of FIG. 42 in use.

FIG. 50 depicts probe 200 in use thermally treating a tissue surface. Direct current power supplied by batteries 218 heats filament wire 236 which also heats air and other gasses in proximity to filament wire 236. RF power from the electrosurgical generator is also applied to filament wire 236. The high temperature of filament 236 increases the ease with which electrons may be ejected from filament 236. Heating of the air and other gases in proximity to filament 236 decreases the resistance of the air and gases to electrical breakdown. These two effects together allow the formation of plasma channels through the air and gases in the gap between filament wire 236 and tissue in close proximity. Power transmitted through these channels interacts with the surface of the tissue thermally treating the tissue and desiccating tissue near the surface. Movement 250 of probe 200 relative to the tissue creates a linear region of treatment, depth 252 of the thermal effect being determined by the applied power and the rate of movement 250.

Figure 51A:
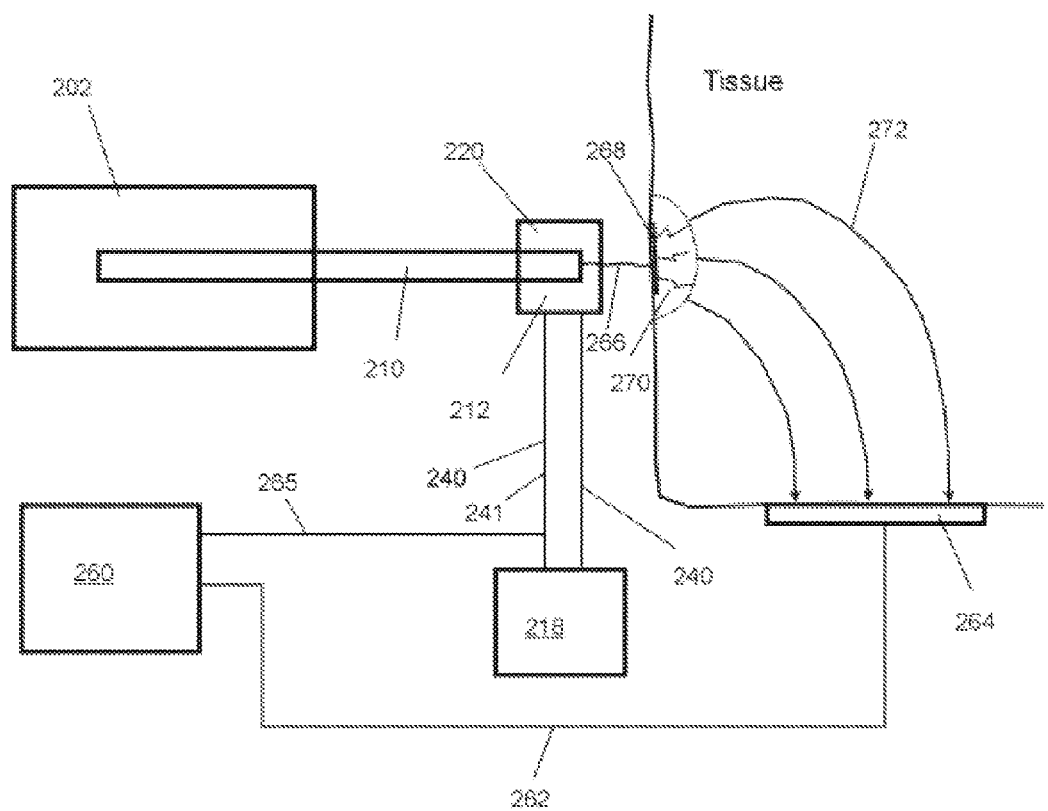
FIG. 51 is a schematic representation of the probe of FIG. 42 in use.
Figure 51B:
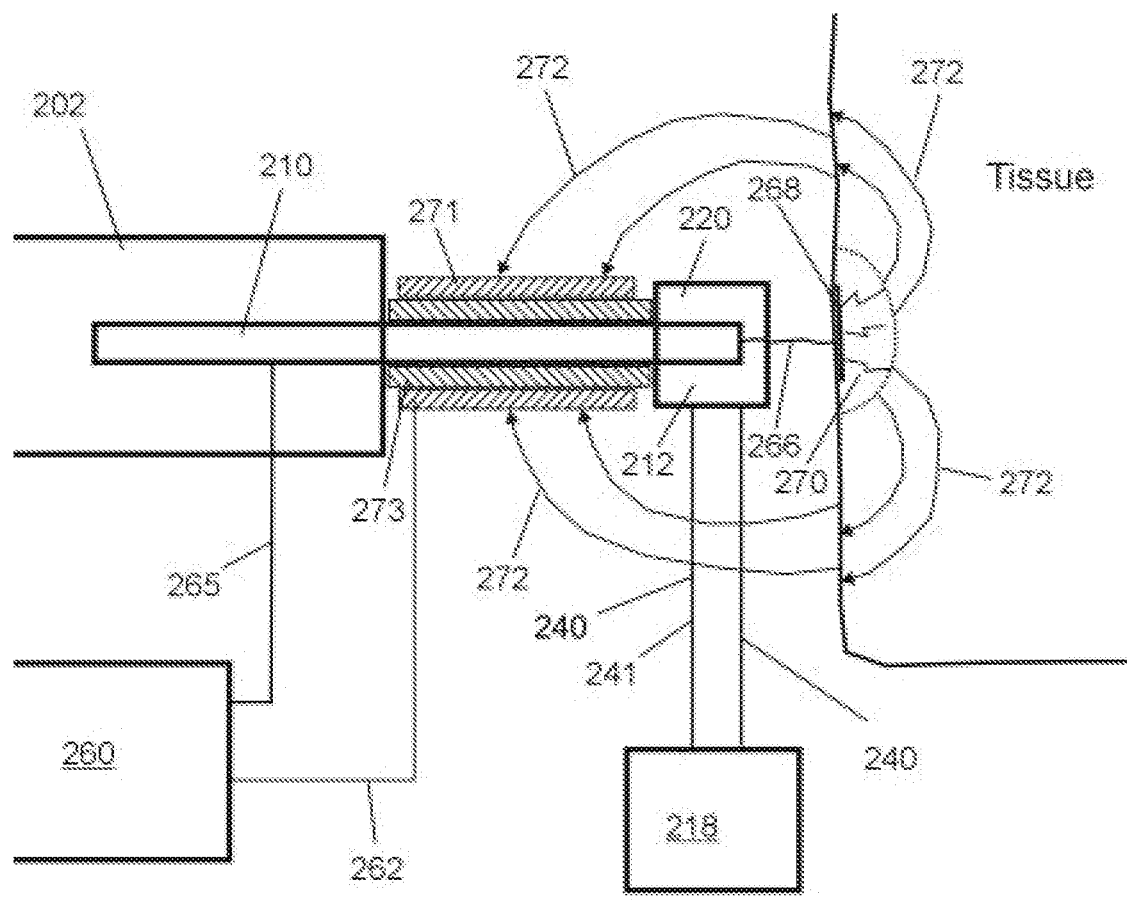

Referring now to FIG. 51 depicting a schematic representation of probe 200 in use, electrosurgical generator 260 is connected by wire 262 to return electrode pad 264, and by wire 265 to first wire 241 of wires 240 connected to batteries 218 and filament 236 in distal end assembly 220. Heating of filament 236 by power from batteries 218 and RF power from generator 260 together produce arcs 266 between filament 236 and tissue in close proximity. Desiccation by heat from arcs 266 creates local layer 268 of dry insulating tissue. Secondary arcing 270 may occur beneath layer 268. Current 272 flows from the region near arcs 266 through the tissue to return electrode 264.

FIG. 52 schematically depicts distal end assembly 220 of probe 200. Batteries 218 via wires 240 and conductive members 238 to filament 236. Wire 265 conducts power from the RF generator to first wire 241 and therefrom via conductive member 238 to filament 236. Power from batteries 218 heats the filament. Power from the RF generator causes arcing 266 and produces the desired clinical effect. FIG. 52 (B) and (C) show that insulator 226 may have a variety of cross-sections. However, those shown are merely illustrative and not intended to limit the scope of the invention.

Figure 53:
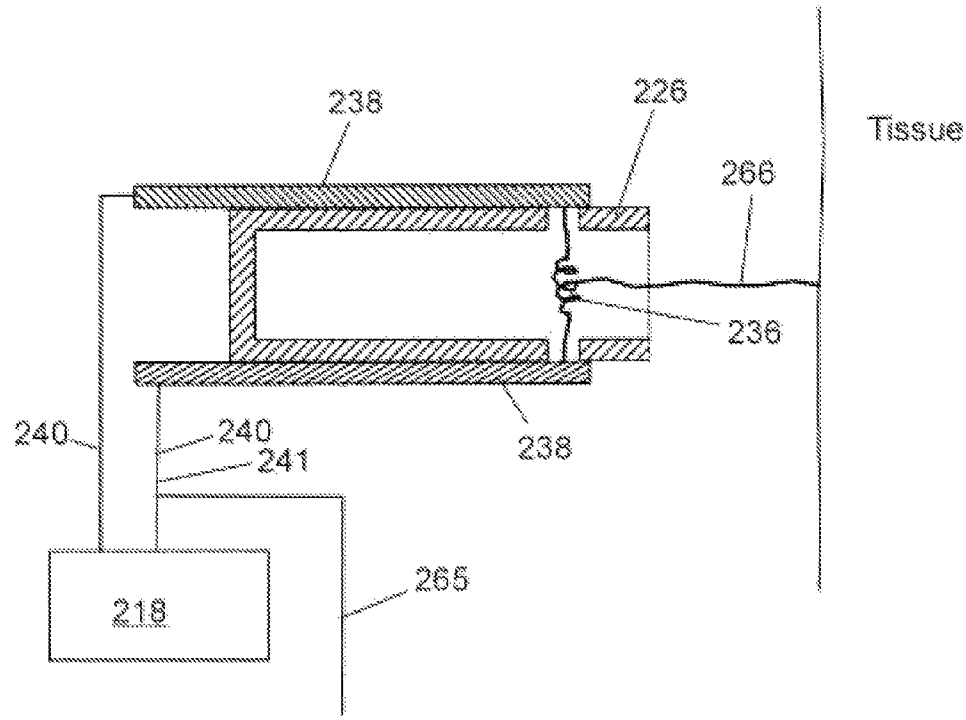
FIG. 53 is a schematic representation of a distal portion of an alternate embodiment having a coil filament.

FIG. 53 depicts an alternate embodiment of distal end assembly 220 of probe 200. Filament 236 has a coil for enhanced heating of the region surrounding filament 236 for increased probe efficiency.

Figure 54:
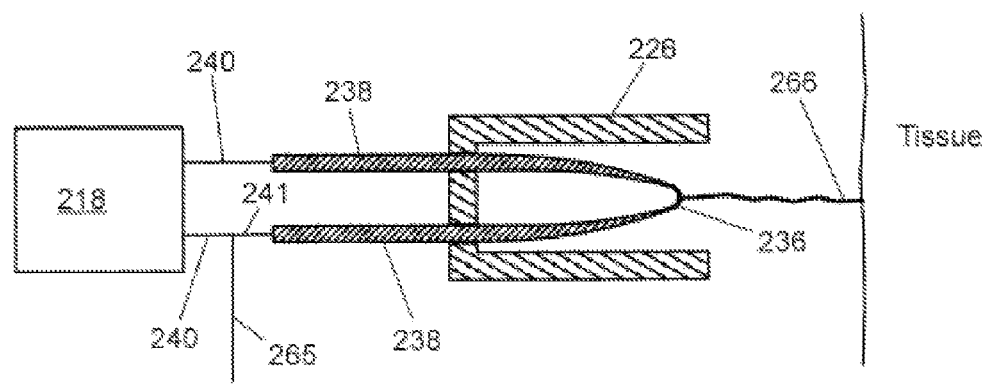
FIG. 54 is a schematic representation of a distal portion of an alternate embodiment having a filament integral with the conductive members.

FIG. 54 depicts an alternate embodiment of distal end assembly 220 of probe 200 in which filament 236 is integral with conductive members 238, the filament portion being of a reduced cross-section.

Figure 55:
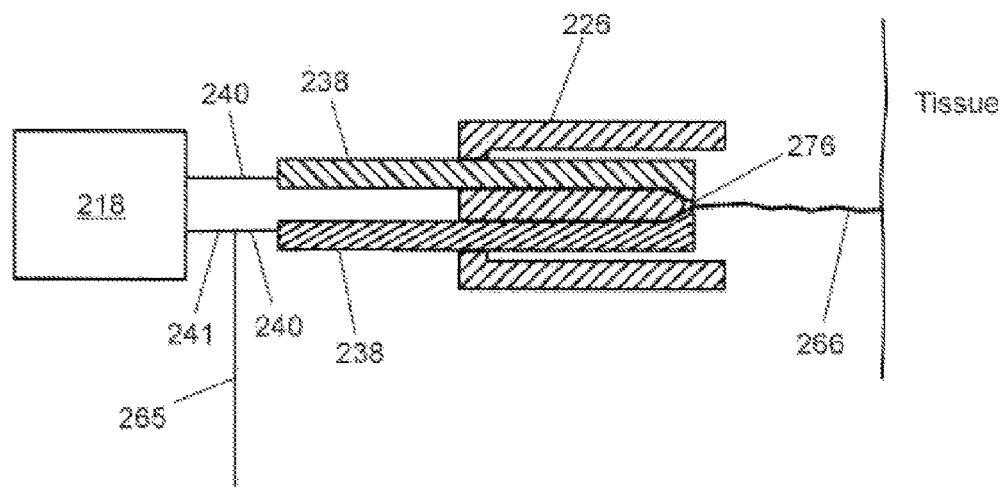
FIG. 55 is a schematic representation of a distal portion of an alternate embodiment which uses micro-sparking between the conductive members rather than a filament.

FIG. 55 depicts an alternate embodiment of distal end assembly 220 of probe 200 in which the filament has been deleted. Conductive members 238 have distal ends which are in sufficiently close proximity to produce micro-arcing 276 therebetween when voltage from power supply 218 is applied.

Figure 56:
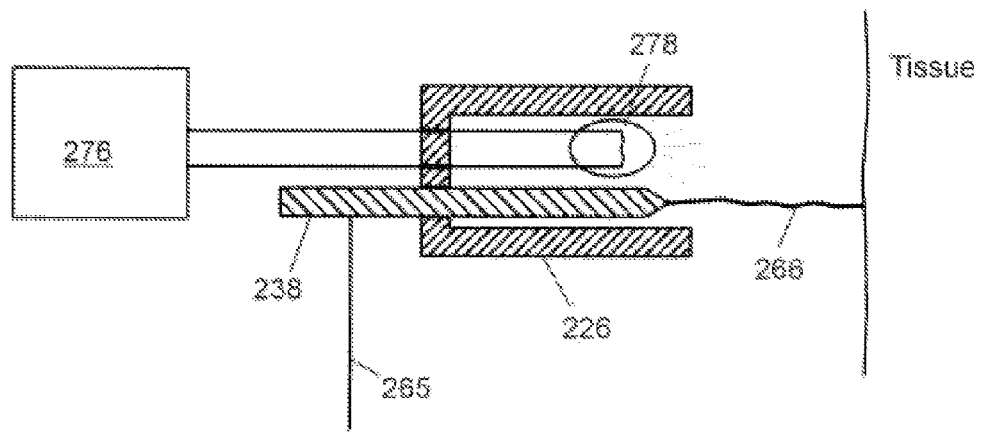
FIG. 56 is a schematic representation of a distal portion of an alternate embodiment which uses a UV lamp as a heat source.

FIG. 56 depicts an alternate embodiment of distal end assembly 220 of probe 200 in which heating at the distal region of the probe is accomplished by a UV lamp 278 connected to power supply 276, rather than by a filament.

Figure 57:
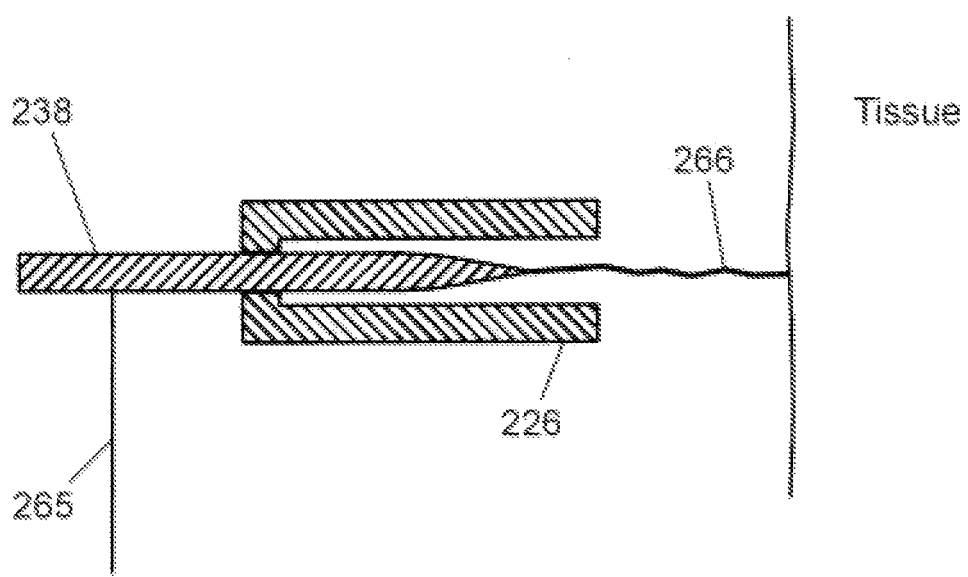
FIG. 57 is a schematic representation of a distal portion of an alternate embodiment which has no filament for micro-sparking.

FIG. 57 depicts an alternate embodiment of distal end assembly 220 of probe 200 in which the conductive member 238 has a sharpened distal end having a low included angle so that the distal portion is heated to an elevated temperature by arcs 266. Heating of the distal portion is enhanced by insulator 226 which closely conforms to member 238 so as to prevent radiant or convective heat loss from member 238.

Figure 58:
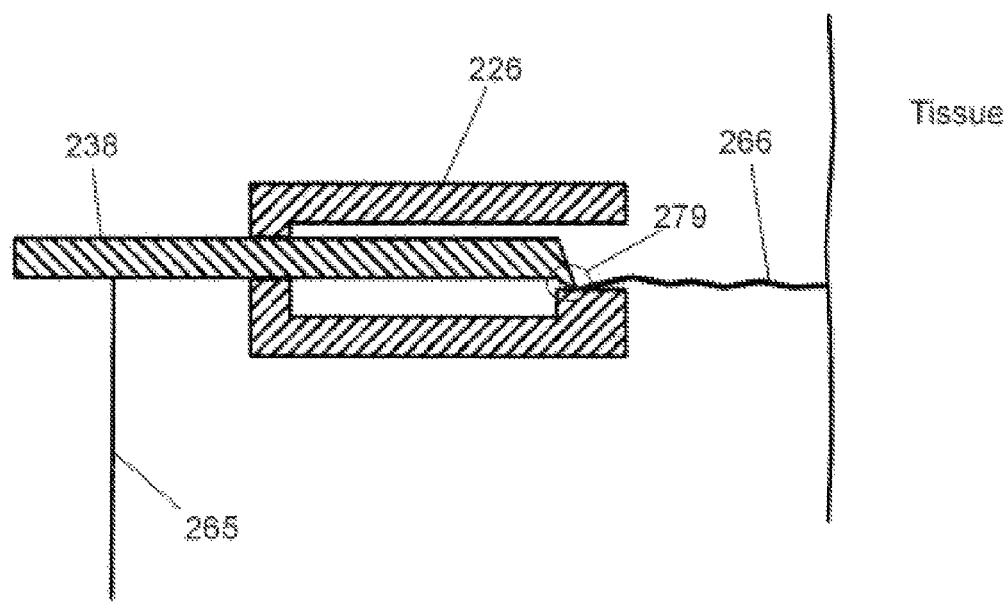
FIG. 58 is a schematic representation of a distal portion of an alternate embodiment which uses dielectric breakdown to produce micro-sparking.

FIG. 58 depicts an alternate embodiment of distal end assembly 220 of probe 200 in which conductive member 238 has a sharpened distal end which is in contact with a portion of insulator 226 such that dielectric breakdown produces micro-sparking which heats the region causing arcs 266 to occur.

Figure 59:
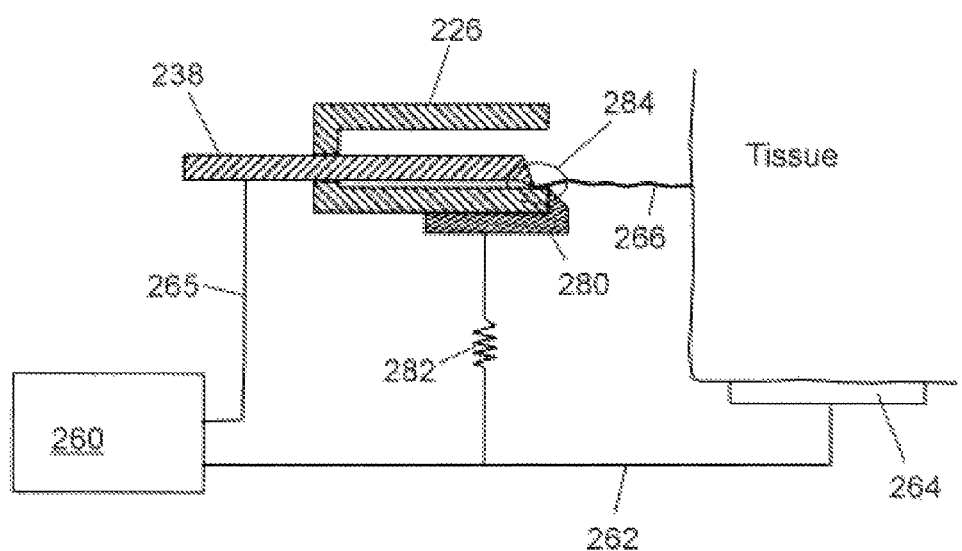
FIG. 59 is a schematic representation of a distal portion of an alternate embodiment which does not use an external power source for micro-sparking or heating a filament.

FIG. 59 depicts an alternate embodiment of distal end assembly 220 of probe 200 in which conductive member 280, connected via resistor 282 to wire 262 of the return electrode circuit, is positioned in close proximity to member 238 such that micro-arcing occurs between members 280 and 238, the micro-arcing producing sufficient heat to allow arcing 266. Resistor 282 limits current through member 280.

As noted above, the embodiment depicted in FIG. 60 corresponds to a new type of minimally invasive instrument, based on miniature, intense sources of infra-red, visible and ultra violet generated by an electrically heated filament mounted inside a disposable instrument. More particularly, FIG. 60 depicts an alternate embodiment of distal end assembly 220 of probe 200 configured for gas flow through the distal portion of probe 200. In FIG. 60(a) gas 292 supplied to nozzle 290 floods the area around filament 236 and arcs 266. In FIG. 60(b) air and gases 294 surrounding arcs 266 and filament 236 are evacuated through nozzle 290.

As noted above, FIG. 61 depicts an alternate embodiment 600 for treating a surface in a body cavity in which a source of electromagnetic energy, which, in this case is a miniature high-intensity infrared lamp 602 is positioned within a transparent inflatable bag 606. The assembly is positioned within a body cavity to be thermally treated. Gas 604 is injected into the bag causing it to inflate and conform to the tissue surface. The IR lamp 602 is energized causing heating of the tissue in contact with the bag 604. Gas flow into and out of the bag is maintained during treatment.

FIG. 62 depicts an alternate embodiment for treating a surface using a probe having at its distal tip 700 a miniature infrared lamp 702, a lens 704 and a reflector 706 for directing heat 708 from the lamp to the tissue surface. The profiles of reflector 706 and lens 704 together determine the energy distribution. In a preferred embodiment the profiles of reflector 706 and lens 704 together produce a uniform distribution across the distal opening of tip 700. In other embodiments, the profiles can cooperate to form distributions such as a concentrated spot, line, annulus, or other predetermined desired profile.

INDUSTRIAL APPLICABILITY

The minimally invasive monopolar and bipolar electrosurgical instruments of the present invention find utility in the area of remote tissue ablation and lesion formation, to destroy tumors, form lesions, denaturize, desiccate, coagulate and ablate soft tissues, as well as to drill, cut, resect and vaporize soft tissues, with or without externally supplied conductive or non-conductive liquids (i.e., in the context of both wet and dry field electrosurgery). More particularly, the electrosurgical instruments of the present invention are designed to heat tissue from the outside in, to provide homogeneous energy deposition using less power, which in turn yields a highly homogeneous lesion.

In this manner, the electrosurgical instruments of the present invention allow one to effectively and efficiently control of the shape and size of the lesion formed, to thereby avoid unnecessary complications and undesired side effects. Such instruments are particularly useful in the context of oncological, ENT, urological, gynecological, and laparascopic procedures, as well as in the context of general surgery.

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention.

Other advantages and features will become apparent from the claims filed hereafter, with the scope of such claims to be determined by their reasonable equivalents, as would be understood by those skilled in the art. Thus, the invention is intended to be defined not by the above description, but by the following claims and their equivalents.

What is claimed is:

1. An electrosurgical instrument for thermal tissue treatment comprising:
 a. an elongate shaft having a proximal end, a distal end and a longitudinal axis, wherein said proximal end is configured for connection to a power source and said a distal end is configured for connection to an electrode assembly;
 b. an electrode assembly mounted to the distal end of said elongate shaft, said electrode assembly comprising:
  i. an insulator formed from a nonconductive dielectric material and comprising discrete proximal and distal portions, wherein said proximal and distal portions comprise opposed walls that extend laterally away from and transverse to said elongate shaft;
  ii. a planar active electrode formed from an electrically conductive material, connected via cabling disposed within said elongate shaft to a power source, and comprising top and bottom surfaces and an edge surface extending therebetween, wherein said active electrode extends between said proximal and distal insulator portions; and
  iii. a floating electrode positioned in close proximity to said active electrode, wherein said floating electrode is formed from an electrically conductive material, is not directly electrically connected to either the elongate shaft or a power source, and shields said top surface and at least a portion of said edge surface of said active electrode; wherein said floating electrode extends between said proximal and distal insulator portions to form an inverted open fluid-fillable cavity in which said active electrode is suspended; and
 c. a tubular member for supplying an irrigant directly to said inverted open fluid-fillable cavity;
 wherein the distalmost end of said active electrode is laterally recessed relative to the distalmost end of the floating electrode;
 further wherein powering of said active electrode in the presence of said irrigant results in flow of current from said active electrode to said floating electrode, heating of said irrigant and generation of steam within said inverted open fluid-fillable cavity, wherein said heated irrigant and steam flow out of said inverted open fluid-fillable cavity and thermally treat target tissue upon contact.

2. The electrosurgical instrument of claim 1, wherein said planar active electrode projects into said insulator distal portion.

3. The electrosurgical instrument of claim 2, wherein said planar active electrode penetrates said proximal insulator portion.

4. The electrosurgical instrument of claim 1, wherein said inverted open fluid-fillable cavity comprises a top portion having two pair of opposed walls depending therefrom.

5. The electrosurgical instrument of claim 4, wherein said opposed insulator walls constitute the first pair of opposed walls of said inverted open fluid-fillable cavity.

6. The electrosurgical instrument of claim 4, wherein said floating electrode comprises a flat base and first and second lateral flanges normal to said flat base that constitute the second pair of opposed walls of said inverted open fluid-fillable cavity.

7. The electrosurgical instrument of claim 6, wherein said tubular member for supplying irrigant includes an irrigation port disposed in the flat base of said floating electrode.

8. The electrosurgical instrument of claim 1, wherein:
   a. said inverted open fluid-fillable cavity comprises a top portion having two pair of opposed walls depending therefrom;
   b. said proximal and distal insulator portions comprise a pair of planar walls that constitute the first pair of opposed walls of said inverted open fluid-fillable cavity;
   c. said floating electrode comprises a flat base and first and second lateral flanges normal to said flat base that constitute the second pair of opposed walls of said inverted open fluid-fillable cavity; and
   d. said tubular member for supplying irrigant comprises a receiving port disposed in the flat base of said floating electrode.

9. The electrosurgical instrument of claim 1, wherein treated tissue comprises tumor tissue.

10. The electrosurgical instrument of claim 1, wherein said thermal treatment results in tumor destruction, lesion formation, or the denaturization, dessication, coagulation or ablation of tumor tissue.

11. The electrosurgical instrument of claim 1, further comprising a return electrode.

12. The electrosurgical instrument of claim 1, wherein said active electrode and floating electrode have radiused lateral edges.

13. A method for thermally treating a target tissue in the body of a patient comprising the step of:
   a. introducing the electrosurgical instrument of claim 1 into the patient such that the electrode assembly is in close contact with the target tissue;
   b. supplying said irrigant to the inverted open fluid-fillable cavity formed by said insulator and said floating electrode; and
   c. applying a high-frequency voltage to said active electrode;
   wherein said high frequency voltage results not only in the flow of current among said active electrode, said floating electrode and said target tissue but further results in the boiling of said irrigant, such that expanding steam and said heated irrigant flow from the inverted open fluid-fillable cavity to the target tissue site, thereby thermally treating said target tissue.

14. The method of claim 13, wherein said instrument further comprises a return electrode disposed thereon.

15. The method of claim 13, wherein said target tissue is a tumor.

16. The method of claim 15, wherein the electrode assembly is placed in direct contact with the surface of the tumor.

17. The method of claim 15, wherein the electrode assembly embedded in the tumor tissue.

18. The method of claim 15, wherein the electrode assembly is provided with a means to facilitate atraumatic insertion into said tumor.

19. The method of claim 15, wherein said means comprises a sharp, tapered conical tip provided at the distal end of said electrode assembly.

20. The method of claim 13, further comprising the step of applying a return electrode to a free surface of tissue near a tumor so as to concentrate current flow between the active and return electrodes, through the tumor.

21. The method of claim 13, wherein said high-frequency voltage comprises RF energy.

22. The method of claim 13, wherein said introduction step (a) is monitored with the use of an external imaging system.

23. The method of claim 22, wherein said imaging system is selected from the group consisting of MRI, CT, PET, ultrasound, x-ray, and fluoroscope.

24. The method of claim 13, wherein the sufficiency of the thermal treatment of said target tissue is determined by means of an external imaging system.

* * * * *